(12) United States Patent
Marsilje et al.

(10) Patent No.: US 8,440,681 B2
(45) Date of Patent: May 14, 2013

(54) 2-BIPHENYLAMINO-4-AMINOPYRIMIDINE DERIVATIVES AS KINASE INHIBITORS

(75) Inventors: Thomas H. Marsilje, San Diego, CA (US); Wenshuo Lu, San Diego, CA (US); Bei Chen, San Diego, CA (US); Xiaohui He, San Diego, CA (US); Badry Bursulaya, Escondido, CA (US); Christian Cho-Hua Lee, San Diego, CA (US)

(73) Assignee: IRM LLC, Hamilton (BM)

( * ) Notice: Subject to any disclaimer, the term of this patent is extended or adjusted under 35 U.S.C. 154(b) by 314 days.

(21) Appl. No.: 12/675,379

(22) PCT Filed: Aug. 27, 2008

(86) PCT No.: PCT/US2008/074392
§ 371 (c)(1),
(2), (4) Date: Aug. 11, 2010

(87) PCT Pub. No.: WO2009/032668
PCT Pub. Date: Mar. 12, 2009

(65) Prior Publication Data
US 2010/0298295 A1    Nov. 25, 2010

Related U.S. Application Data

(60) Provisional application No. 61/075,556, filed on Jun. 25, 2008.

(51) Int. Cl.
*A61K 31/4965* (2006.01)
*A61K 31/497* (2006.01)
*C07D 239/48* (2006.01)

(52) U.S. Cl.
USPC .......................... 514/275; 544/323; 544/324

(58) Field of Classification Search .................. 514/275; 544/323
See application file for complete search history.

(56) References Cited

U.S. PATENT DOCUMENTS

| 2006/0270694 A1 | 11/2006 | Wong |
| 2008/0176881 A1 | 7/2008 | Michellys et al. |
| 2011/0112063 A1 | 5/2011 | Marsilje et al. |
| 2011/0112096 A1 | 5/2011 | Marsilje et al. |

FOREIGN PATENT DOCUMENTS

| WO | 2000/012485 A1 | 3/2000 |
| WO | 01/07027 A2 | 2/2001 |
| WO | 0160816 A1 | 8/2001 |
| WO | 01/64655 A1 | 9/2001 |
| WO | 03/018021 A1 | 3/2003 |
| WO | 03/026664 A1 | 4/2003 |
| WO | 03/026666 A1 | 4/2003 |
| WO | 03/078404 A1 | 9/2003 |
| WO | 2004/080980 A1 | 9/2004 |
| WO | 2004087698 A2 | 10/2004 |
| WO | 2005/016893 A2 | 2/2005 |
| WO | 2005/016894 A1 | 2/2005 |
| WO | 2005/026130 A1 | 3/2005 |
| WO | 2005/026158 A1 | 3/2005 |
| WO | 2006/074057 A2 | 7/2006 |
| WO | 2006/137706 A1 | 12/2006 |
| WO | 2007/027238 A2 | 3/2007 |
| WO | 2007/031829 A2 | 3/2007 |
| WO | 2007053452 A1 | 5/2007 |
| WO | 2008/005538 A2 | 1/2008 |
| WO | 2008/015250 A1 | 2/2008 |
| WO | 2008/051547 A1 | 5/2008 |
| WO | 2008/073687 A2 | 6/2008 |
| WO | 2008/083465 A1 | 7/2008 |
| WO | 2008/127349 A2 | 10/2008 |
| WO | 2009/017838 A2 | 2/2009 |
| WO | 2009/067081 A1 | 5/2009 |
| WO | 2009/103652 A1 | 8/2009 |

OTHER PUBLICATIONS

Thornber, 1979, Chem. Soc. Rev., vol. 8, p. 563-580.*

* cited by examiner

*Primary Examiner* — Wu-Cheng Winston Shen
*Assistant Examiner* — Karen Cheng
(74) *Attorney, Agent, or Firm* — Emily Tongco Wu; Genomics Institute of the Novartis Research Foundation

(57) ABSTRACT

The invention provides novel pyrimidine derivatives of formula (1) and pharmaceutical compositions thereof, and methods for using such compounds. For example, the pyrimidine derivatives of the invention may be used to treat, ameliorate or prevent a condition which responds to inhibition of insulin-like growth factor (IGF-1R) or anaplastic lymphoma kinase (ALK).

(1)

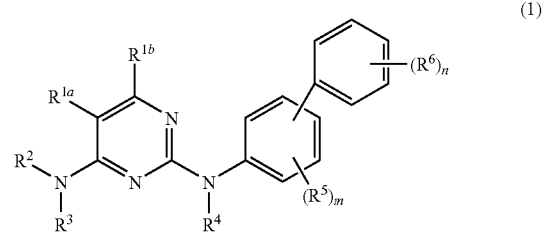

7 Claims, No Drawings

2-BIPHENYLAMINO-4-AMINOPYRIMIDINE DERIVATIVES AS KINASE INHIBITORS

CROSS-REFERENCE TO RELATED APPLICATIONS

This application is a 371 U.S. national phase application of international application number PCT/US2008/074392 filed 27 Aug. 2008, which application claims the benefit of U.S. provisional patent application No. 61/075,556, filed 25 Jun. 2008. The full disclosure of these applications is incorporated herein by reference in their entirety and for all purposes.

TECHNICAL FIELD

The invention relates to protein kinase inhibitors, more particularly novel pyrimidine derivatives and pharmaceutical compositions thereof, and their use as pharmaceuticals.

BACKGROUND ART

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life. Sci. 61:2939-2953 (2004)).

Because of the emerging disease-related roles of IGF-1R and ALK, there is a continuing need for compounds which may be useful for treating and preventing a disease which responds to inhibition of IGF-1R and ALK.

DISCLOSURE OF THE INVENTION

The invention relates to novel pyrimidine derivatives and pharmaceutical compositions thereof, and their use as pharmaceuticals.

In one aspect, the invention provides compounds of Formula (1):

(1)

or a pharmaceutically acceptable salt thereof;
wherein $R^{1a}$ is H, halo, $OR^8$, $NR(R^8)$, $SR^8$; $C_{1-6}$ alkyl, $C_{1-6}$alkoxy, $C_{2-6}$ alkenyl or $C_{2-6}$ alkynyl, each of which may be optionally substituted with halo, amino or hydroxyl groups; $C(O)R^8$, $NC(O)R^9$, $C(O)NRR^8$, $S(O)_2NRR^8$, $NS(O)_2R^9$, $S(O)_{0-2}R^9$; or an optionally substituted $C_{3-12}$ carbocyclic ring, $C_{6-10}$ aryl; or a 5-10 membered heteroaryl or heterocyclic ring containing 1-4 heteroatoms selected from N, O and S;

$R^{1b}$ is H or $NH_2$;

$R^2$ is an optionally substituted $C_{6-10}$ carbocyclic, or a 5-10 membered heteroaryl or 5-7 membered heterocyclic ring each having 1-3 heteroatoms selected from N, O and S;

$R^3$ and $R^4$ are independently H, $C(O)R^7$, $C_{1-6}$ alkyl or halo-substituted $C_{1-6}$ alkyl;

$R^5$, $R^6$ and $R^7$ are independently $C_{1-6}$ alkyl, $C_{1-6}$alkoxy, $C_{2-6}$ alkenyl or $C_{2-6}$ alkynyl, each of which may be optionally substituted with halo, amino or hydroxyl groups; or $R^5$, $R^6$ and $R^7$ are independently halo, nitro, cyano, $OR^8$, $O(CR_2)_p$—$OR^8$, -L-NR($R^8$), -L-NR($CR_2)_p OR^8$, -L-NR—$(CR_2)_q$—C(O)$R^9$, -L-Y, -L-C(O)O$_{0-1}$—$(CR_2)_q$—$R^8$, -L-C(O)—NRR$^8$, -L-C(O)—NR—$(CR_2)_p$—NRR$^8$, -L-C(O)NR($CR_2)_p OR^8$, -L-C(O)—$(CR_2)_q$—NR—C(O)—$R^9$, -L-C(O)NR($CR_2)_p$SR$^8$, -L-C(O)NR($CR_2)_p$S(O)$_{1-2}R^9$, -L-S(O)$_2R^9$, -L-S(O)$_2$NRR$^8$, -L-S(O)$_2$NR($CR_2)_p$NR($R^8$), -L-S(O)$_2$NR($CR_2)_p$OR$^8$;

wherein L is $(CR_2)_{1-4}$ or a bond;

alternatively, two adjacent $R^5$ groups together with the carbon atoms they are attached to may form an optionally substituted 9-14 membered ring;

$R^7$, $R^8$ and $R^9$ are independently $(CR_2)_q Y$ or $C_{1-6}$ alkyl, $C_{1-6}$ alkoxy, $C_{2-6}$ alkenyl or $C_{2-6}$ alkynyl, each of which may be optionally substituted with halo, amino or hydroxyl; or $R^7$ and $R^8$ are independently H;

each R is H or $C_{1-6}$ alkyl;

Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $R^6$ groups;

m and p are independently 1-4; and
n and q are independently 0-4.

In particular examples, $R^{1b}$ in the above Formula (1) is H. In some examples, m is 2-4; or more particularly, m is 2.

In one embodiment, the invention provides compounds of Formula (2A) or (2B):

(2A)

(2B)

wherein one of $R^{5a}$, $R^{5b}$ and $R^{5c}$ is H and the others and $R^6$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{5a}$, $R^b$, $R^{5c}$ and $R^6$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)$O_{0-1}$—$(CR_2)_q$—$R^8$, -L-C(O)—$NRR^8$, -L-C(O)—NR—$(CR_2)_p$—$NRR^8$, -L-C(O)$NR(CR_2)_pOR^8$, -L-C(O)—$(CR_2)_q$—NR—C(O)—$R^9$, -L-C(O)$NR(CR_2)_pSR^8$, -L-C(O)$NR(CR_2)_pS(O)_{1-2}R^9$, -L-S(O)$_2R^9$, -L-S(O)$_2NRR^8$, -L-S(O)$_2NR(CR_2)_pNR(R^8)$, -L-S(O)$_2NR(CR_2)_pOR^8$; wherein L is $(CR_2)_{1-4}$ or a bond; and R, $R^{1a}$, $R^2$, $R^3$, $R^4$, $R^8$, $R^9$, Y, p and q are as defined in Formula (1).

In some examples, $R^{5b}$ in the above Formula (2A) or (2B) is H; and $R^{5a}$ and $R^{5c}$ are independently halo, hydroxyl, $C_{1-6}$ alkyl, $C_{1-6}$ alkoxy, halo-substituted $C_{1-6}$ alkyl or halo-substituted $C_{1-6}$ alkoxy. In particular examples, $R^{5b}$ is H; $R^{5a}$ is halo, hydroxyl, $C_{1-6}$ alkoxy or $C_{1-6}$ alkyl; and $R^{5c}$ is halo, $C_{1-4}$ alkyl, or halo-substituted $C_{1-6}$ alkyl. In other examples, $R^{5c}$ is H; and $R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy.

In another embodiment, the invention provides compounds of Formula (3A) or (3B):

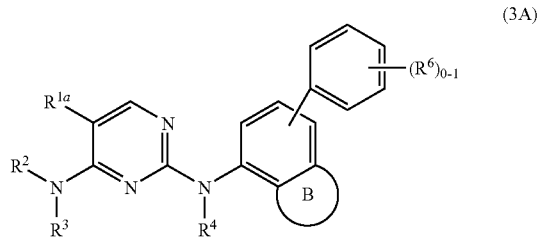

(3A)

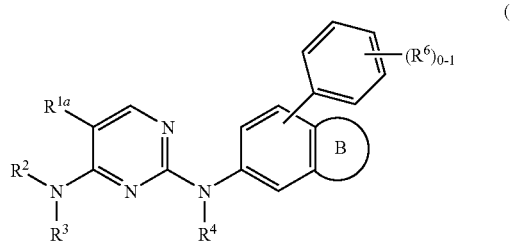

(3B)

wherein ring B is an optionally substituted $C_{5-7}$ carbocyclic ring, $C_{6-10}$ aryl; or a 5-membered heteroaryl or 5-7 membered heterocyclic ring; and $R^{1a}$, $R^2$, $R^3$, $R^4$ and $R^6$ are as defined in Formula (1).

In the above Formula (1), (2A), (2B), (3A) and (3B), $R^2$ may be pyrazolyl, pyrrolyl, thiophenyl, pyrimidinyl, isoxazolyl, pyridyl, azepan-2-onyl, thiazolyl, imidazolyl, isoxazolyl, indazolyl, quinolinyl, cyclohexyl, or bicycle[2.2.1]hept-5-enyl, each of which may be optionally substituted with 1-2 $R^6$ groups. In some examples, $R^2$ may be substituted with $C_{1-6}$ alkyl, -L-Y, -L-C(O)$O_{0-1}$—$(CR_2)_q$—$R^8$ or -L-C(O)—$NRR^8$, wherein L is $(CR_2)_{1-4}$ or a bond and R, $R^8$, Y and q are as defined above.

In the above Formula (1), (2A), (2B), (3A) and (3B), $R^6$ may be $C_{1-6}$ alkyl, -L-NR-L-C(O)$R^9$, -L-C(O)$O_{0-1}$—$(CR_2)_q$—$R^8$, -L-C(O)—$NRR^8$, -L-S(O)$_2R^9$ or -L-S(O)$_2NRR^8$, wherein R, $R^8$ and $R^9$ are as defined above.

In another aspect, the invention provides compounds of Formula (4):

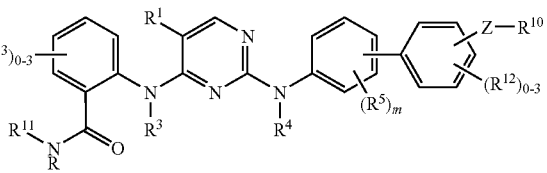

(4)

or pharmaceutically acceptable salts thereof;

wherein $R^1$ is H, halo, $OR^8$, $NR(R^8)$, $SR^8$; $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; $C(O)R^8$, $NC(O)R^9$, $C(O)NRR^8$, $S(O)_2NRR^8$, $NS(O)_2R^9$, $S(O)_{0-2}R^9$; or an optionally substituted $C_{3-12}$ carbocyclic ring, $C_{6-10}$ aryl; or a 5-10 membered heteroaryl or heterocyclic ring containing 1-4 heteroatoms selected from N, O and S;

$R^3$ and $R^4$ are independently H, $C(O)R^7$, $C_{1-6}$ alkyl or halo-substituted $C_{1-6}$ alkyl;

$R^5$, $R^{12}$ and $R^{13}$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^5$, $R^{12}$ and $R^{13}$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)$O_{0-1}$—$(CR_2)_q$—$R^8$, -L-C(O)—$NRR^8$, -L-C(O)—NR—$(CR_2)_p$—$NRR^8$, -L-C(O)$NR(CR_2)_pOR^8$, -L-C(O)—$(CR_2)_q$—NR—C(O)—$R^9$, -L-C(O)$NR(CR_2)_pSR^8$, -L-C(O)$NR(CR_2)_pS(O)_{1-2}R^9$, -L-S(O)$_2R^9$, -L-S(O)$_2NRR^8$, -L-S(O)$_2NR(CR_2)_pNR(R^8)$, -L-S(O)$_2NR(CR_2)_pOR^8$; wherein L is $(CR_2)_{1-4}$ or a bond;

$R^7$, $R^8$, $R^9$ and $R^{11}$ are independently $(CR_2)_qY$ or $C_{1-6}$ alkyl, $C_{1-6}$ alkoxy, $C_{2-6}$ alkenyl or $C_{2-6}$ alkynyl, each of which may be optionally substituted with halo, amino or hydroxyl; or $R^7$, $R^8$ and $R^{11}$ are independently H;

$R^{10}$ is $NR(R^8)$, $NR(CR_2)_pNR(R^8)$, $NR(CR_2)_pOR^8$, $NR(CR_2)_qC(O)R^8$ or $R^9$;

each R is H or $C_{1-6}$ alkyl;

Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $R^5$ groups;

Z is CO or $S(O)_{1-2}$;

m and p are independently 1-4; and q is 0-4.

In some examples, m in the above Formula (4) is 2-4. In particular examples, m is 2.

In one embodiment, the invention provides compounds of Formula (4A):

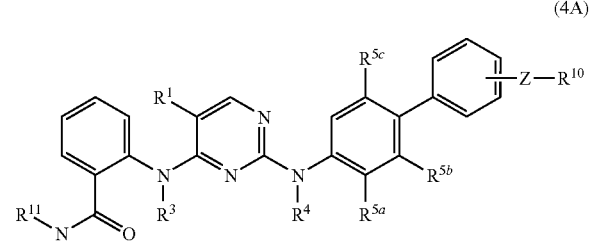

(4A)

wherein one of $R^{5a}$, $R^{5b}$ and $R^{5c}$ is H and the others are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{5a}$, $R^{5b}$ and $R^{5c}$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)$O_{0-1}$—$(CR_2)_q$—$R^8$, -L-C(O)—$NRR^8$, -L-C(O)—NR—$(CR_2)_p$—$NRR^8$, -L-C(O)$NR(CR_2)_pOR^8$, -L-C(O)—$(CR_2)_q$—NR—C(O)—$R^9$, -L-C(O)$NR(CR_2)_pSR^8$, -L-C(O)$NR(CR_2)_pS(O)_{1-2}R^9$, -L-S(O)$_2R^9$, -L-S(O)$_2NRR^8$, -L-S(O)$_2NR(CR_2)_pNR(R^8)$, -L-S(O)$_2NR(CR_2)_pOR^8$; wherein L is $(CR_2)_{1-4}$ or a bond; and R, $R^1$, $R^3$, $R^4$, $R^8$, $R^9$, $R^{10}$, $R^{11}$, Y, Z, p and q are as defined in Formula (4).

In some examples, $R^{5b}$ in the above Formula (4A) is H; and $R^{5a}$ and $R^{5c}$ are independently halo, hydroxyl, $C_{1-6}$ alkyl, $C_{1-6}$ alkoxy, halo-substituted $C_{1-6}$ alkyl, halo-substituted $C_{1-6}$ alkoxy or -L-C(O)$O_{0-1}$—$(CR_2)_q$—$R^8$;

wherein L is a bond;
$R^8$ is $(CR_2)_qY$;
each q is 0; and
Y is a 5-7 membered heterocyclic ring.

In the above Formula (1), (2A), (2B), (3A), (3B), (4) and (4A), $R^{1a}$ may be halo, $C_{1-6}$ alkyl, or a halo-substituted $C_{1-6}$ alkyl. In other examples, $R^3$ is H or CO($R^7$) wherein $R^7$ is $C_{1-6}$ alkyl; and $R^4$ is H. In particular examples, $R^3$ and $R^4$ are H.

In yet another aspect, the present invention provides pharmaceutical compositions comprising a compound having Formula (1), (2A), (2B), (3A), (3B), (4) or (4A), and a pharmaceutically acceptable excipient.

Furthermore, the invention provides methods for inhibiting IGF1R or ALK, or for treating a condition mediated by IGF1R or ALK, comprising administering to a cell or tissue system or to a mammalian subject, a therapeutically effective amount of a compound of Formula (1), (2A), (2B), (3A), (3B), (4) or (4A), or pharmaceutically acceptable salts or tautomers thereof, and optionally in combination with a second therapeutic agent; thereby inhibiting said kinase or treating said condition mediated by IGF1R or ALK.

The invention also provides methods to treat, ameliorate or prevent a condition which responds to inhibition of IGF-1R or ALK, comprising administering to a system or subject in need of such treatment an effective amount of a compound having Formula (1), (2A), (2B), (3A), (3B), (4) or (4A), or pharmaceutically acceptable salts or pharmaceutical compositions thereof, and optionally in combination with a second therapeutic agent, thereby treating said condition. Alternatively, the present invention provides the use of a compound having Formula (1), (2A), (2B), (3A), (3B), (4) or (4A), in the manufacture of a medicament for treating a condition mediated by IGF-1R or ALK. In particular embodiments, the compounds of the invention may be used alone or in combination with a second therapeutic agent to treat a condition mediated by IGF-1R or ALK, wherein said condition is an autoimmune disease, a transplantation disease, an infectious disease or a cell proliferative disorder.

Furthermore, the invention provides methods for treating a cell proliferative disorder, comprising administering to a system or subject in need of such treatment an effective amount of a compound having Formula (1), (2A), (2B), (3A), (3B), (4) or (4A), or pharmaceutically acceptable salts or pharmaceutical compositions thereof, and optionally in combination with a second therapeutic agent, thereby treating said condition. Alternatively, the present invention provides the use of a compound having Formula (1), (2A), (2B), (3A), (3B), (4) or (4A), in the manufacture of a medicament for treating a cell proliferative disorder. In particular examples, the compounds of the invention may be used alone or in combination with a chemotherapeutic agent to treat a cell proliferative disorder, including but not limited to, multiple myeloma, neuroblastoma, synovial, hepatocellular, Ewing's Sarcoma or a solid tumor selected from a osteosarcoma, melanoma, and tumor of breast, renal, prostate, colorectal, thyroid, ovarian, pancreatic, lung, uterine or gastrointestinal tumor.

In the above methods for using the compounds of the invention, a compound having Formula (1), (2A), (2B), (3A), (3B), (4) or (4A), may be administered to a system comprising cells or tissues, or to a mammalian subject such as a human or animal subject.

DEFINITIONS

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. For example, a heteroaryl substituent for use in the compounds of the invention may be a monocyclic or bicyclic 5-10 membered heteroaryl containing 1-4 heteroatoms selected from N, O, and S. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring for use in the compounds of the invention may be a 4-7 membered heterocyclic ring containing 1-3 heteroatoms selected from N, O and S, or a combination thereof such as —S(O) or —S(O)$_2$—. Examples of heterocyclic rings include but are not limited to azetidinyl, morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

As used herein, an H atom in any substituent groups (e.g., $CH_2$) encompasses all suitable isotopic variations, e.g., H, $^2H$ and $^3H$.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the invention and prodrugs thereof to a subject in need of treatment.

MODES OF CARRYING OUT THE INVENTION

The invention provides novel pyrimidine derivatives and pharmaceutical compositions thereof, and methods for using such compounds.

In one aspect, the invention provides compounds of Formula (1):

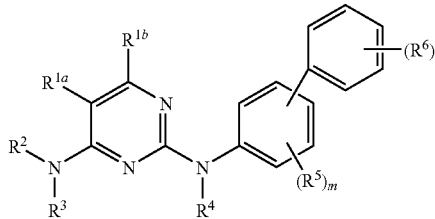

(1)

or a pharmaceutically acceptable salt thereof;

wherein $R^{1a}$ is H, halo, $OR^8$, $NR(R^8)$, $SR^8$; $C_{1-6}$ alkyl, $C_{1-6}$alkoxy, $C_{2-6}$ alkenyl or $C_{2-6}$ alkynyl, each of which may be optionally substituted with halo, amino or hydroxyl groups; $C(O)R^8$, $NC(O)R^9$, $C(O)NRR^8$, $S(O)_2NRR^8$, $NS(O)_2R^9$, $S(O)_{0-2}R^9$; or an optionally substituted $C_{3-12}$ carbocyclic ring, $C_{6-10}$ aryl; or a 5-10 membered heteroaryl or heterocyclic ring containing 1-4 heteroatoms selected from N, O and S;

$R^{1b}$ is H or $NH_2$;

$R^2$ is an optionally substituted $C_{6-10}$ carbocyclic, or a 5-10 membered heteroaryl or 5-7 membered heterocyclic ring each having 1-3 heteroatoms selected from N, O and S;

$R^3$ and $R^4$ are independently H, $C(O)R^7$, $C_{1-6}$ alkyl or halo-substituted $C_{1-6}$ alkyl;

$R^5$, $R^6$ and $R^7$ are independently $C_{1-6}$ alkyl, $C_{1-6}$alkoxy, $C_{2-6}$ alkenyl or $C_{2-6}$ alkynyl, each of which may be optionally substituted with halo, amino or hydroxyl groups; or $R^5$, $R^6$ and $R^7$ are independently halo, nitro, cyano, $OR^8$, $O(CR_2)_p$—$OR^8$, -L-$NR(R^8)$, -L-$NR(CR_2)_pOR^8$, -L-NR—$(CR_2)_q$—C(O)$R^9$, -L-Y, -L-C(O)$O_{0-1}$—$(CR_2)_q$—$R^8$, -L-C(O)—$NRR^8$, -L-C(O)—NR—$(CR_2)_p$—$NRR^8$, -L-C(O)NR$(CR_2)_pOR^8$, -L-C(O)—$(CR_2)_q$—NR—C(O)—$R^9$, -L-C(O)NR$(CR_2)_p$SR$^8$, -L-C(O)NR$(CR_2)_pS(O)_{1-2}R^9$, -L-S(O)$_2R^9$, -L-S(O)$_2$NRR$^8$, -L-S(O)$_2$NR$(CR_2)_pNR(R^8)$, -L-S(O)$_2NR(CR_2)_pOR^8$; wherein L is $(CR_2)_{1-4}$ or a bond;

alternatively, two adjacent $R^5$ groups together with the carbon atoms they are attached to may form an optionally substituted 9-14 membered ring;

$R^7$, $R^8$ and $R^9$ are independently $(CR_2)_qY$ or $C_{1-6}$ alkyl, $C_{1-6}$ alkoxy, $C_{2-6}$ alkenyl or $C_{2-6}$ alkynyl, each of which may be optionally substituted with halo, amino or hydroxyl; or $R^7$ and $R^8$ are independently H;

each R is H or $C_{1-6}$ alkyl;

Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $R^6$ groups;

m and p are independently 1-4; and n and q are independently 0-4.

In one embodiment, the invention provides compounds of Formula (2A) or (2B):

(2A)

(2B)

wherein one of $R^{5a}$, $R^{5b}$ and $R^{5c}$ is H and the others and $R^6$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{5a}$, $R^b$, $R^{5c}$ and $R^6$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)$O_{0-1}$—$(CR_2)_q$—$R^8$, -L-C(O)—$NRR^8$, -L-C(O)—NR—$(CR_2)_p$—$NRR^8$, -L-C(O)NR$(CR_2)_pOR^8$, -L-C(O)—$(CR_2)_q$—NR—C(O)—$R^9$, -L-C(O)NR$(CR_2)_p$SR$^8$, -L-C(O)NR$(CR_2)_pS(O)_{1-2}R^9$, -L-S(O)$_2R^9$, -L-S(O)$_2$NRR$^8$, -L-S(O)$_2NR(CR_2)_pNR(R^8)$, -L-S(O)$_2NR(CR_2)_pOR^8$; wherein L is $(CR_2)_{1-4}$ or a bond; and R, $R^{1a}$, $R^2$, $R^3$, $R^4$, $R^8$, $R^9$, Y, p and q are as defined in Formula (1).

In another embodiment, the invention provides compounds of formula (3A) or (3B):

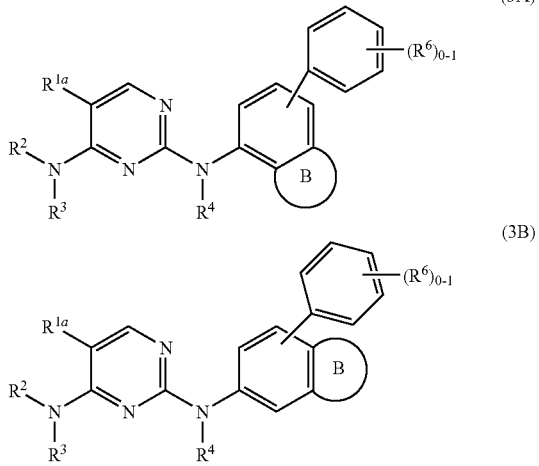

wherein ring B is an optionally substituted $C_{5-7}$ carbocyclic ring, $C_{6-10}$ aryl; or a 5-10 membered heteroaryl or 5-7 membered heterocyclic ring; and $R^{1a}$, $R^2$, $R^3$, $R^4$ and $R^6$ are as defined in Formula (1).

In another aspect, the invention provides compounds of Formula (4):

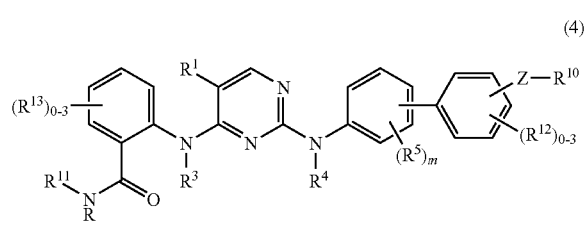

or pharmaceutically acceptable salts thereof;

wherein $R^1$ is H, halo, $OR^8$, $NR(R^8)$, $SR^8$; $C_{1-6}$ alkyl, $C_{1-6}$alkoxy, $C_{2-6}$ alkenyl or $C_{2-6}$ alkynyl, each of which may be optionally substituted with halo, amino or hydroxyl groups; $C(O)R^8$, $NC(O)R^9$, $C(O)NRR^8$, $S(O)_2NRR^8$, $NS(O)_2R^9$, $S(O)_{0-2}R^9$; or an optionally substituted $C_{3-12}$ carbocyclic ring, $C_{6-10}$ aryl; or a 5-10 membered heteroaryl or heterocyclic ring containing 1-4 heteroatoms selected from N, O and S;

$R^3$ and $R^4$ are independently H, $C(O)R^7$, $C_{1-6}$ alkyl or halo-substituted $C_{1-6}$ alkyl;

$R^5$, $R^{12}$ and $R^{13}$ are independently $C_{1-6}$ alkyl, $C_{1-6}$alkoxy, $C_{2-6}$ alkenyl or $C_{2-6}$ alkynyl, each of which may be optionally substituted with halo, amino or hydroxyl groups; or $R^5$, $R^{12}$ and $R^{13}$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)O$_{0-1}$—$(CR_2)_q$—$R^8$, -L-C(O)—$NRR^8$, -L-C(O)—NR—$(CR_2)_p$—$NRR^8$, -L-C(O)NR$(CR_2)_pOR^8$, -L-C(O)—$(CR_2)_q$—NR—C(O)—$R^9$, -L-C(O)NR$(CR_2)_p$SR$^8$, -L-C(O)NR$(CR_2)_p$S(O)$_{1-2}R^9$, -L-S(O)$_2R^9$, -L-S(O)$_2$NRR$^8$, -L-S(O)$_2$NR$(CR_2)_p$NR(R$^8$), -L-S(O)$_2$NR$(CR_2)_p$OR$^8$;
wherein L is $(CR_2)_{1-4}$ or a bond;

$R^7$, $R^8$, $R^9$ and $R^{11}$ are independently $(CR_2)_qY$ or $C_{1-6}$ alkyl, $C_{1-6}$alkoxy, $C_{2-6}$ alkenyl or $C_{2-6}$ alkynyl, each of which may be optionally substituted with halo, amino or hydroxyl; or $R^7$, $R^8$ and $R^{11}$ are independently H;

$R^{10}$ is $NR(R^8)$, $NR(CR_2)_pNR(R^8)$, $NR(CR_2)_pOR^8$, $NR(CR_2)_qC(O)R^8$ or $R^9$;

each R is H or $C_{1-6}$ alkyl;

Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $R^5$ groups;

Z is CO or $S(O)_{1-2}$;

m and p are independently 1-4; and q is 0-4.

In one embodiment, the invention provides compounds of Formula (4A):

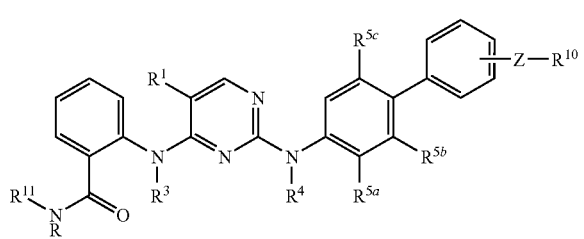

wherein one of $R^{5a}$, $R^{5b}$ and $R^{5c}$ is H and the others are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{5a}$, $R^{5b}$ and $R^{5c}$ are independently halo, nitro, cyano, $OR^8$, $O(CR_2)_p$—$OR^8$, -L-$NR(R^8)$, -L-$NR(CR_2)_pOR^8$, -L-NR-L-C(O)$R^9$, -L-Y, -L-C(O)O$_{0-1}$—$(CR_2)_q$—$R^8$, -L-C(O)—$NRR^8$, -L-C(O)—NR—$(CR_2)_p$—$NRR^8$, -L-C(O)NR$(CR_2)_pOR^8$, -L-C(O)—$(CR_2)_q$—NR—C(O)—$R^9$, -L-C(O)NR$(CR_2)_p$SR$^8$, -L-C(O)NR$(CR_2)_p$S(O)$_{1-2}R^9$, -L-S(O)$_2R^9$, -L-S(O)$_2$NRR$^8$, -L-S(O)$_2$NR$(CR_2)_p$NR(R$^8$), -L-S(O)$_2$NR$(CR_2)_p$OR$^8$; wherein L is $(CR_2)_{1-4}$ or a bond; and R, $R^1$, $R^3$, $R^4$, $R^8$, $R^9$, $R^{10}$, $R^{11}$, Y, Z, p and q are as defined in Formula (4).

In the above Formula (1), (2A), (2B), (3A) or (3B), examples of 5-10 membered heteroaryl or 5-7 membered heterocyclic ring $R^2$ groups include but are not limited to pyrazolyl, pyrrolyl, thiophenyl, pyrimidinyl, isoxazolyl, pyridyl, azepan-2-onyl, 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2-oxazine, 4H-1,2-oxazine, 6H-1,2-oxazine, 2H-1,3-oxazine, 4H-1,3-oxazine, 4H-1,4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane. 1,2,4-trioxolane, 1,2,3-triazoline and 1,2,3-triazolidine.

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies.

In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl$C_1$-$C_8$alkyl, $C_1$-$C_8$alkoxy$C_1$-$C_8$alkyl); halo, amino, amidino, $C_{1-6}$ alkoxy; hydroxyl, methylenedioxy, carboxy; $C_{1-8}$ alkylcarbonyl, $C_{1-8}$ alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, the compounds of the invention may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [γ-$^{33}$P]-ATP, 2 µM ATP, 3 µg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

The compounds of the invention may potently inhibit the growth of human NPM-ALK overexpressing murine BaF3 cells (DSMZ Deutsche Sammlung von Mikroorganismen and Zellkulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

In another aspect, the compounds of the invention may inhibit insulin like growth-factor receptor 1 (IGF-1R). The efficacy of the compounds of the invention as inhibitors of IGF-1R kinase activity may be demonstrated using a cellular capture ELISA. In this assay, the activity of the compounds of the invention against (IGF-1)-induced autophosphorylation of the IGF-1R is determined.

The compounds of the invention may be useful in the treatment of IGF-1R and/or ALK mediated diseases. Examples of IGF-1R and/or ALK mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas.

The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), s inflammatory eye diseases, e.g. Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;

(2) a compound of the invention for use as an IGF-1R inhibitor, for example for use in any of the particular indications hereinbefore set forth;

(3) a pharmaceutical composition, e.g. for use in any of the indications herein before set forth, comprising a compound of the invention as active ingredient together with one or more pharmaceutically acceptable diluents or carriers;

(4) a method for the treatment of any particular indication set forth hereinbefore in a subject in need thereof which comprises administering an effective amount of a compound of the invention or a pharmaceutical composition comprising same;

(5) the use of a compound of the invention for the manufacture of a medicament for the treatment or prevention of a disease or condition in which IGF-1R activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;

(7) a combination comprising a therapeutically effective amount of a compound of the invention and one or more further drug substances, said further drug substance being useful in any of the particular indications set forth hereinbefore;

(8) use of a compound of the invention for the manufacture of a medicament for the treatment or prevention of a disease which responds to inhibition of the anaplastic lymphoma kinase;

(9) the use according to (8), wherein the disease to be treated is selected from anaplastic large cell lymphoma, non-Hodgkin's lymphomas, inflammatory myofibroblastic tumors, neuroblastomas and neoplastic diseases;

(10) the use according to (8) or (9), wherein the compound is or a pharmaceutically acceptable; salt of any one of the examples;

(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.01 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the invention may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, bras sidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length $C_8$ to $C_{12}$ from Hills AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the invention may be administered as the sole active ingredient, or together with other drugs useful against neoplastic diseases or useful in immunomodulating regimens. For example, the compounds of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T.

W. Greene and P. G. M. Wuts in "Protective Groups in Organic Chemistry", John Wiley and Sons, 1991).

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of Formula (1), (2A), (2B), (3A), (3B), (4) and (4A) may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2A), (2B), (3A), (3B), (4) and (4A) with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", $3^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

Intermediate 1

2,5-dichloro-N-(5-methyl-1H-pyrazol-3-yl)pyrimidin-4-amine

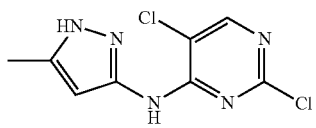

A mixture of 5-methyl-1H-pyrazol-3-amine (3.00 g, 30.9 mmol), 2,4,5-trichloropyrimidine (5.67 g, 30.9 mmol, 1 equiv.) and Na$_2$CO$_3$ (3.60 g, 34.0 mmol, 1.1 equiv.) in EtOH (100 mL) is heated at 40° C. for 24 h. The solvent is removed in vacuo. The resulting residue is partitioned between EtOAc (350 mL) and water (100 mL). The EtOAc layer is washed with water (3×), saturated aqueous NaCl (1×) and dried over Na$_2$SO$_4$. The resulting EtOAc solution is concentrated in vacuo, providing the product 2,5-dichloro-N-(5-methyl-1H-pyrazol-3-yl)pyrimidin-4-amine; ESMS m/z 244.0 (M+H$^+$).

Intermediate 2

2-chloro-5-methyl-N-(5-methyl-1H-pyrazol-3-yl)pyrimidin-4-amine

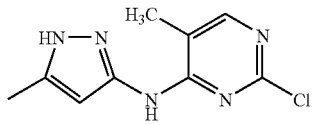

A mixture of 5-methyl-1H-pyrazol-3-amine (3.00 g, 30.9 mmol), 2,4-dichloro-5-methylpyrimidine (5.03 g, 30.9 mmol, 1 equiv.) and Na$_2$CO$_3$ (3.60 g, 34.0 mmol, 1.1 equiv.) in EtOH (100 mL) is heated at 40° C. for 24 h. The solvent is removed in vacuo. The resulting residue is partitioned between EtOAc (350 mL) and water (100 mL). The EtOAc layer is washed with water (3×), saturated aqueous NaCl (1×), dried over Na$_2$SO$_4$, and concentrated in vacuo. The resulting crude product is sonicated in Et$_2$O (200 mL) and the resulting precipitate collected by filtration. This powder is further washed with Et$_2$O, providing the product 2-chloro-5-methyl-N-(5-methyl-1H-pyrazol-3-yl)pyrimidin-4-amine; ESMS m/z 224.1 (M+H$^+$).

Intermediate 3

2-(2,5-dichloropyrimidin-4-ylamino)benzamide

A mixture of 2-aminobenzamide (681 mg, 5.0 mmol), 2,4,5-trichloropyrimidine (2.75 g, 15 mmol, 3 equiv.) and concentrated HCl (aq) (1.72 mL, 20 mmol, 4 equiv.) in 2-propanol (100 mL) is heated at 60° C. for 12 h. The 2-propanol solvent is removed in vacuo. The resulting residue is neutralized to approximately pH=7 by adding 1 N NaOH (aq) followed by partition between EtOAc and water. Upon partition between EtOAc and water, a significant amount of precipitate is produced. This precipitate is collected by vacuum filtration and washed with small amounts of EtOAc and water, providing the product 2-(2,5-dichloropyrimidin-4-ylamino)benzamide; ESMS m/z 283.0 (M+H$^+$).

Intermediate 4

3-(2,5-dichloropyrimidin-4-ylamino)pyridin-2(1H)-one

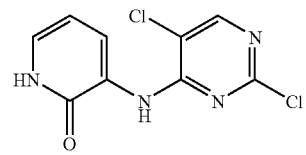 [SMILES: O=c1[nH]cccc1Nc1nc(Cl)ncc1Cl]

A mixture of 3-aminopyridin-2(1H)-one (99 mg, 0.90 mmol), 2,4,5-trichloropyrimidine (165 mg, 0.90 mmol, 1 equiv.) and NaHCO$_3$ (76 mg, 0.90 mmol, 1 equiv.) in a mixture of MeOH (6 mL) and H$_2$O (3 mL) is stirred at room temperature for 24 h. The resulting precipitate is collected by vacuum filtration and washed with small amounts of MeOH and water, providing the product 3-(2,5-dichloropyrimidin-4-ylamino)pyridin-2(1H)-one; ESMS m/z 257.0 (M+H$^+$).

Intermediate 5

(±)-cis-2-(2,5-dichloropyrimidin-4-ylamino)cyclohexanecarboxamide

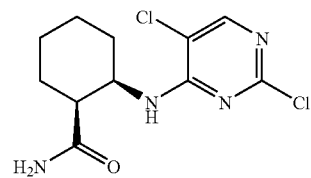 [SMILES: NC(=O)[C@H]1CCCC[C@H]1Nc1nc(Cl)ncc1Cl]

A mixture of (±)-cis-2-aminocyclohexanecarboxamide (28 mg, 0.20 mmol), 2,4,5-trichloropyrimidine (37 mg, 0.20 mmol, 1 equiv.) and NaHCO$_3$ (17 mg, 0.20 mmol, 1 equiv.) in a mixture of MeOH (1.0 mL) and H$_2$O (0.5 mL) is stirred at room temperature for 12 h. The reaction is diluted with EtOAc and washed with water (2×), dried over Na$_2$SO$_4$ and concentrated in vacuo to generate the product (±)-cis-2-(2,5-dichloropyrimidin-4-ylamino)cyclohexanecarboxamide; ESMS m/z 289.1 (M+H$^+$).

Intermediate 6

2,5-Dichloro-N-(5-phenyl-1H-pyrazol-3-yl)pyrimidin-4-amine

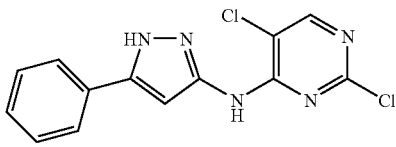 [SMILES: Clc1ncc(Cl)c(Nc2cc(-c3ccccc3)[nH]n2)n1]

The mixture of 3-amino-5-phenylpyrazole (103 mg, 0.65 mmol), 2,4,5-trichloropyrimidine (74.5 µL, 0.65 mmol), and sodium carbonate (68.9 mg, 0.65) in 3 mL of EtOH is heated at 40° C. over night. The precipitate is filtered, washed by cold EtOH, and dried in vacuo to afford 2,5-Dichloro-N-(5-phenyl-1H-pyrazol-3-yl)pyrimidin-4-amine; ESMS m/z 306.0 (M+H$^+$).

Intermediate 7

Methyl 4-(2,5-dichloropyrimidin-4-ylamino)-1-methyl-1H-pyrrole-2-carboxylate

The mixture of 4-amino-1-methyl-pyrrole-2-carboxylic acid methyl ester hydrochloride (95 mg, 0.5 mmol), 2,4,5-trichloropyrimidine (57 µL, 0.5 mmol), and sodium carbonate (106 mg, 1.0 mmol) in 3 mL of EtOH is heated at 40° C. overnight. The precipitate is filtered, washed by cold EtOH, and dried in vacuo to afford methyl 4-(2,5-dichloropyrimidin-4-ylamino)-1-methyl-1H-pyrrole-2-carboxylate; ESMS m/z 301.0 (M+H$^+$).

Intermediate 8

2-(2,5-Dichloropyrimidin-4-ylamino)-4-methylthiophene-3-carboxamide

The mixture of 2-amino-4-methylthiophene-3-carboxamide (78 mg, 0.5 mmol), 2,4,5-trichloropyrimidine (57 µL, 0.5 mmol), and sodium carbonate (53 mg, 0.5 mmol) in 3 mL of EtOH is heated at 40° C. over night. The precipitate is filtered, washed by cold EtOH, and dried in vacuo to afford 2-(2,5-Dichloropyrimidin-4-ylamino)-4-methylthiophene-3-carboxamide; ESMS m/z 303.0 (M+H$^+$).

Intermediate 9

N-(2,5-Dichloropyrimidin-4-yl)pyrimidin-2-amine

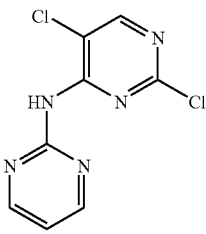 [SMILES: Clc1ncc(Cl)c(Nc2ncccn2)n1]

The mixture of pyrimidin-2-amine (48 mg, 0.50 mmol), 2,4,5-trichloropyrimidine (57 µL, 0.5 mmol), and potassium carbonate (69 mg, 0.5 mmol) in 3 mL of 1,4-dioxane is heated at 110° C. over night. The precipitate is filtered, washed by cold EtOH, and dried in vacuo to afford N-(2,5-Dichloropyrimidin-4-yl)pyrimidin-2-amine; ESMS m/z 242.0 (M+H$^+$).

Intermediate 10

2,5-Dichloro-N-(1-methyl-1H-pyrazol-3-yl)pyrimidin-4-amine

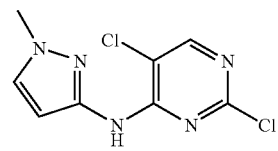

The mixture 1-methyl-1H-pyrazol-3-amine (48 mg, 0.50 mmol), 2,4,5-trichloropyrimidine (57 µL, 0.5 mmol), and sodium carbonate (53 mg, 0.5 mmol) in 3 mL of EtOH is heated at 40° C. over night. The precipitate is filtered, washed by cold EtOH, and dried in vacuo to afford 2,5-Dichloro-N-(1-methyl-1H-pyrazol-3-yl)pyrimidin-4-amine; ESMS m/z 244.0 (M+H$^+$).

Intermediate 11

Ethyl 3-(2,5-dichloropyrimidin-4-ylamino)-1H-pyrazole-4-carboxylate

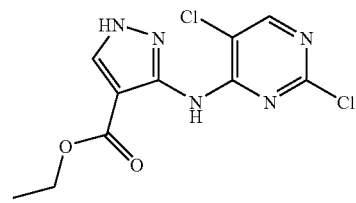 [SMILES: CCOC(=O)c1c[nH]nc1Nc1nc(Cl)ncc1Cl]

The mixture ethyl 3-amino-1H-pyrazole-4-carboxylate (80 mg, 0.50 mmol), 2,4,5-trichloropyrimidine (57 µL, 0.5 mmol), and sodium carbonate (53 mg, 0.5 mmol) in 3 mL of EtOH is heated at 40° C. over night. The precipitate is filtered, washed by cold EtOH, and dried in vacuo to afford ethyl 3-(2,5-dichloropyrimidin-4-ylamino)-1H-pyrazole-4-carboxylate; ESMS m/z 302.0 (M+H$^+$).

Intermediate 12

N-(2,5-Dichloropyrimidin-4-yl)isoxazol-3-amine

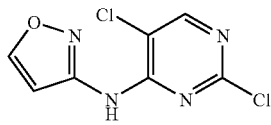

The mixture isoxazol-3-amine (36 μL, 0.50 mmol), 2,4,5-trichloropyrimidine (57 μL, 0.5 mmol), and sodium carbonate (53 mg, 0.5 mmol) in 3 mL of EtOH is heated at 60° C. for 48 hrs. The precipitate is filtered, washed by cold EtOH, and dried in vacuo to afford N-(2,5-Dichloropyrimidin-4-yl)isoxazol-3-amine; ESMS m/z 231.0 (M+H$^+$).

Intermediate 13

2,5-Dichloro-N-(4,6-dimethylpyridin-2-yl)pyrimidin-4-amine

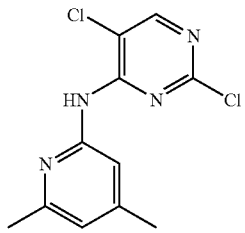 [SMILES: Cc1cc(C)nc(Nc2nc(Cl)ncc2Cl)c1]

The mixture 4,6-dimethylpyridin-2-amine (61 mg, 0.50 mmol), 2,4,5-trichloropyrimidine (57 μL, 0.5 mmol), and potassium iodide (166 mg, 1.0 mmol) in 3 mL of DMA is heated at 90° C. overnight. The mixture is concentrated in vacuo and the resulting crude product is partitioned between EtOAc and brine. The collected organic extracts are dried (Na$_2$SO$_4$) and concentrated in vacuo to afford 2,5-dichloro-N-(4,6-dimethylpyridin-2-yl)pyrimidin-4-amine; ESMS m/z 269.0 (M+H$^+$).

Intermediate 14

N-(2,5-dichloropyrimidin-4-yl)-5-methylisoxazol-3-amine

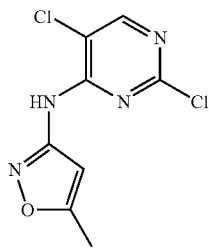

The mixture 5-methylisoxazol-3-amine (98 mg, 1.0 mmol), 2,4,5-trichloropyrimidine (344 μL, 3.0 mmol), and sodium carbonate (106 mg, 1.0 mmol) in 3 mL of EtOH is heated at 60° C. over night. The reaction mixture is concentrated and then partitioned between EtOAc and brine. The collected organic extracts are dried (Na$_2$SO$_4$), concentrated in vacuo, and purified with silica gel chromatography (MeOH/DCM: 1/9) to afford N-(2,5-dichloropyrimidin-4-yl)-5-methylisoxazol-3-amine; ESMS m/z 245.0 (M+H$^+$).

Intermediate 15

2,5-dichloro-N-(5-cyclopropyl-1H-pyrazol-3-yl)pyrimidin-4-amine

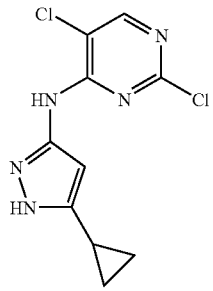 [SMILES: Clc1ncc(Cl)c(Nc2cc(C3CC3)[nH]n2)n1]

A mixture of 5-cyclopropyl-1H-pyrazol-3-amine (246 mg, 2.00 mmol), 2,4,5-trichloropyrimidine (367 mg, 2.00 mmol, 1 equiv.) and Na$_2$CO$_3$ (233 mg, 2.20 mmol, 1.1 equiv.) in EtOH (10 mL) is heated at 40° C. for 16 h. The crude reaction mixture is diluted with EtOAc and sequentially washed with: water (3×) and saturated aqueous NaCl (1×). The resulting EtOAc layer is dried over Na$_2$SO$_4$ and then concentrated in vacuo, providing 2,5-dichloro-N-(5-cyclopropyl-1H-pyrazol-3-yl)pyrimidin-4-amine; ESMS m/z 270.0 (M+H$^+$).

Intermediate 16

3-(2,5-dichloropyrimidin-4-ylamino)azepan-2-one

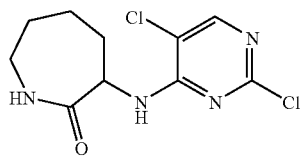 [SMILES: O=C1NCCCCC1Nc1nc(Cl)ncc1Cl]

A mixture of (±)-α-amino-ε-caprolactam (256 mg, 2.0 mmol), 2,4,5-trichloropyrimidine (366 mg, 2.0 mmol, 1 equiv.) and NaHCO$_3$ (168 mg, 2 mmol, 1 equiv.) in a mixture of MeOH (12 mL) and H$_2$O (6 mL) is stirred at room temperature for 15 h. The resulting precipitate is collected by vacuum filtration and washed with small amounts of MeOH and water, providing the product 3-(2,5-dichloropyrimidin-4-ylamino)azepan-2-one; ESMS m/z 275.0 (M+H$^+$).

Intermediate 17

4'-Amino-5'-fluoro-N,2'-dimethylbiphenyl-4-carboxamide

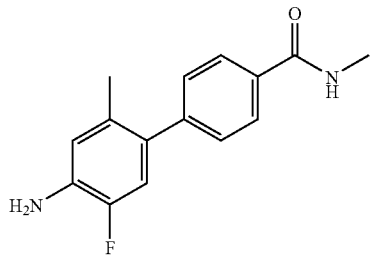 [SMILES: CNC(=O)c1ccc(-c2cc(F)c(N)cc2C)cc1]

The mixture of 4-bromo-2-fluoro-5-methylaniline (203 mg, 1.0 mmol), 4-(methylcarbamoyl)phenylboronic acid (179 mg, 1.0 mmol), 2-dicyclohexylphosphino-2',6'-dimethoxybiphenyl (82 mg, 0.2 mmol), Pd$_2$(dba)$_3$ (91 mg, 0.1 mmol), and K$_3$PO$_4$ (424 mg, 2.0 mmol) in 5.0 mL of n-butanol is degassed and heated at 130° C. for 1 h. The reaction mixture is concentrated in vacuo. The crude product mixture is partitioned between EtOAc and brine, the collected organic extracts are dried (Na$_2$SO$_4$), concentrated and purified with silica gel chromatography (EtOAc/hexanes:1/4) to afford 4'-amino-5'-fluoro-N,2'-dimethylbiphenyl-4-carboxamide; ESMS m/z 259.1 (M+H$^+$).

Intermediate 18

4'-amino-2'-isopropyl-N,5'-dimethylbiphenyl-4-carboxamide

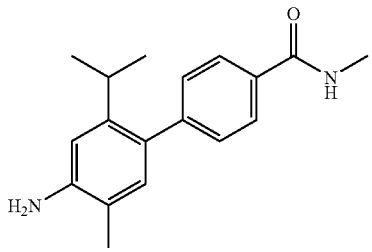 [SMILES: CNC(=O)c1ccc(-c2cc(C)c(N)cc2C(C)C)cc1]

Step 1: 2-isopropyl-5-methylphenyl trifluoromethanesulfonate

To a stirred solution of 2-isopropyl-5-methylphenol (1 g, 6.67 mmol) and triethylamine (2.8 mL, 20 mmol) in DCM (50 mL) is added N-phenyl bis-trifluoromethane sulfonamide (2.62 g, 7.3 mmol). The mixture is stirred for 12 h and concentrated. The residue is purified with silica gel chromatography (5% ethyl acetate in hexanes) to afford 2-isopropyl-5-methylphenyl trifluoromethanesulfonate as colorless oil.

Step 2: 2-isopropyl-5-methyl-4-nitrophenyl trifluoromethanesulfonate

To a solution of 2-isopropyl-5-methylphenyl trifluoromethanesulfonate (Step 1, 1.3 g, 4.6 mmol) in acetic acid (10 mL) is slowly added conc. sulfuric acid and conc. nitric acid premixed solution (2 mL/0.5 mL) at 0° C. After stifling at room temperature for 2 hours, the mixture is poured into ice water. The mixture is extracted with ethyl acetate (3×20 mL). The combined organic phase is washed with sodium carbonate aqueous solution and brine, and dried over sodium sulfate. After concentration, the crude 2-isopropyl-5-methyl-4-nitrophenyl trifluoromethanesulfonate is used directly in the next step without purification.

Step 3: 2'-isopropyl-N,5'-dimethyl-4'-nitrobiphenyl-4-carboxamide

To a mixture of crude 2-isopropyl-5-methyl-4-nitrophenyl trifluoromethanesulfonate (Step 2, 200 mg, 0.61 mmol), 4-(methylcarbamoyl)phenylboronic acid (142 mg, 0.79 mmol) and cesium fluoride (185 mg, 1.22 mmol) in dioxane (15 mL), is added palladium bis(tri-tert-butylphospine) (15 mg, 10% mmol) in a microwave tube. The tube is sealed. The mixture is purged with N$_2$ for 3 min, and then heated at 120° C. for 10 min under microwave irradiation. The mixture is cooled, filtered and concentrated. The residue is purified with silica gel chromatography (60% ethyl acetate in hexanes) to afford white solid as 2'-isopropyl-N,5'-dimethyl-4'-nitrobiphenyl-4-carboxamide. ESMS m/z 313.2 (M+H$^+$).

Step 4: 4'-amino-2'-isopropyl-N,5'-dimethylbiphenyl-4-carboxamide

2'-isopropyl-N,5'-dimethyl-4'-nitrobiphenyl-4-carboxamide is dissolved in methanol (20 mL). To this solution is added Pd/C (10%). The reaction mixture is degassed and purged with H$_2$ for several times and then stirred under H$_2$ (1 atm.) overnight. The mixture is filtered and concentrated to afford the title compound 4'-amino-2'-isopropyl-N,5'-dimethylbiphenyl-4-carboxamide as a white solid. $^1$H NMR (400 MHz, MeOD-d4) δ 7.87 (d, 2H, J=8.4 Hz), 7.35 (d, 2H, J=8.4 Hz), 7.31 (s, 1H), 7.14 (s, 1H), 3.00 (m, 1H), 2.95 (d, 3H), 2.36 (s, 3H), 1.15 (d, 6H, J=6.8 Hz); ESMS m/z 283.2 (M+H$^+$).

Intermediate 19

4'-amino-5'-ethyl-N,2'-dimethylbiphenyl-4-carboxamide

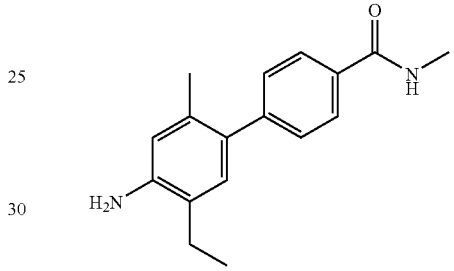

Step 1: 1-Bromo-5-chloro-2-methyl-4-nitrobenzene

Following the procedure previously described (Intermediate 18, Step 2) using 2-bromo-4-chloro-1-methylbenzene generates 1-Bromo-5-chloro-2-methyl-4-nitrobenzene as yellow solid. This material is used in the next step without additional purification.

Step 2: 5'-chloro-N,2'-dimethyl-4'-nitrobiphenyl-4-carboxamide

To a mixture of the crude product from Step 1 (400 mg, 1.6 mmol), 4-(methylcarbamoyl)phenylboronic acid (286 mg, 1.6 mmol) and sodium carbonate (340 mg, 3.2 mmol) in dimethoxylethane/water (12/4 mL), is added palladium tetrakis(triphenylphospine) (93 mg, 5% mmol). The mixture is purged with N$_2$ for 3 min, then sealed and heated at 90° C. for 3 h. The mixture is cooled, filtered and concentrated. The residue is purified with silica gel chromatography (30% ethyl acetate in DCM) to afford 5'-chloro-N,2'-dimethyl-4'-nitrobiphenyl-4-carboxamide as yellow solid. ESMS m/z 305.1 (M+H$^+$).

Steps 3 and 4: 4'-amino-5'-ethyl-N,2'-dimethylbiphenyl-4-carboxamide

To a mixture of 5'-chloro-N,2'-dimethyl-4'-nitrobiphenyl-4-carboxamide (Step 2, 100 mg, 0.33 mmol), vinylboronic acid dibutyl ester (90 mg, 0.5 mmol) and sodium carbonate (245 mg, 2.31 mmol) in THF/H$_2$O (8/2 mL) is added dichlorobis(triphenylphospine) palladium (II) (12 mg, 5% mmol). The reaction tube is sealed, the mixture is purged with N$_2$ for 3 min and then heated at 90° C. under N$_2$ for overnight. The reaction is cooled to room temperature and poured into saturated aqueous ammonia chloride solution. The crude reaction mixture is extracted with ethyl acetate (3×15 mL). The organic extracts are combined, washed with brine and concentrated. The crude product is purified with silica gel column chromatography (30% ethyl acetate in DCM) to afford N,2'-dimethyl-4'-nitro-5'-vinylbiphenyl-4-carboxamide as a yellow solid. The obtained solid is dissolved in methanol (20 mL). To this solution is added Pd/C (10%). The reaction mixture is degassed and purged with H$_2$ for several times and stirred under atmospheric hydrogen overnight. The mixture is filtered and concentrated to afford 4'-amino-5'-ethyl-N,2'-dimethylbiphenyl-4-carboxamide as a yellow solid. ESMS m/z 269.2 (M+H$^+$).

Intermediate 20

4-(4-amino-5,6,7,8-tetrahydronaphthalen-1-yl)-N-methylbenzamide

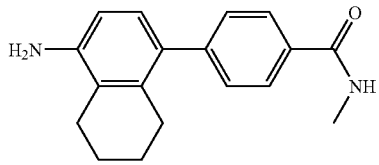 [SMILES: CNC(=O)c1ccc(-c2ccc(N)c3c2CCCC3)cc1]

4-bromo-5,6,7,8-tetrahydronaphthalen-1-amine

To a solution of 5,6,7,8-tetrahydronaphthalen-1-amine (1 g, 6.8 mmol), triethylamine (1.9 mL, 13.6 mmol) in DCM (50 mL), is added acetyl chloride (587 mg, 7.5 mmol) dropwise. The mixture is stirred at room temperature for 2 hr. Then the mixture is concentrated and partitioned between ethyl acetate and saturated aqueous ammonium chloride. The organic layer is separated, washed with brine and dried over sodium sulfate. After concentration, the obtained N-(5,6,7,8-tetrahydronaphthalen-1-yl)acetamide (200 mg) is dissolved in acetic acid (30 mL). To this solution is added bromine (170 mg, 1.06 mmol) dropwise. The mixture is heated at 50° C. overnight. The reaction is quenched by adding sodium sulfite aqueous solution. The mixture is extracted with ethyl acetate (3×20 mL). The organic extracts are combined and washed with sodium bicarbonate aqueous solution, brine, and dried over sodium sulfate. After concentration, the crude N-(4-bromo-5,6,7,8-tetrahydronaphthalen-1-yl)acetamide is obtained as brown solid. The solid obtained is dissolved in methanol (5 mL) and concentrated HCl (15 mL). The mixture is refluxed at 95° C. overnight. After cooling to room temperature, the mixture is poured into ice water, and basified to pH=12 with conc. NaOH aqueous solution. Then the mixture is extracted with ethyl acetate (3×20 mL). The combined organic layer is dried over Na$_2$SO$_4$ and concentrated. The crude product is purified with silica gel chromatography (15% ethyl acetate in hexanes) to give 4-bromo-5,6,7,8-tetrahydronaphthalen-1-amine as beige solid. ESMS m/z 226 (M+H$^+$).

Following the procedures previously described (Intermediate 17) using the product from Step 3 generates 4-(4-amino-5,6,7,8-tetrahydronaphthalen-1-yl)-N-methylbenzamide as a white solid, ESMS m/z 281.2 (M+H$^+$).

Intermediate 21

Methyl 4-amino-5-methoxy-4'-(methylcarbamoyl)biphenyl-2-carboxylate

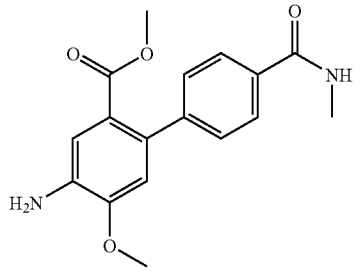 [SMILES: CNC(=O)c1ccc(-c2cc(OC)c(N)cc2C(=O)OC)cc1]

Step 1: Methyl 5-methoxy-4'-(methylcarbamoyl)-4-nitrobiphenyl-2-carboxylate

Under nitrogen, the mixture of methyl 2-chloro-4-methoxy-5-nitrobenzoate (292 mg, 1.19 mmol), 4-(methylcarbamoyl)phenylboronic acid (319 mg, 1.79 mmol), dichlorobis(triphenylphosphine)palladium (II) (41 mg, 0.06 mmol) and sodium carbonate (378 mg, 3.57 mmol) in THF (8 mL) and water (2 mL) is heated at 40° C. overnight. The reaction mixture is cooled to room temperature and then partitioned between EtOAc and brine. The organic extracts are dried (Na$_2$SO$_4$), concentrated in vacuo, and purified by silica gel chromatography (EtOAc/Hexanes:1/3) to afford Methyl 5-methoxy-4'-(methylcarbamoyl)-4-nitrobiphenyl-2-carboxylate; ESMS m/z 345.1 (M+H$^+$).

Step 2: Methyl 4-amino-5-methoxy-4'-(methylcarbamoyl)biphenyl-2-carboxylate

The mixture of methyl 5-methoxy-4'-(methylcarbamoyl)-4-nitrobiphenyl-2-carboxylate (Step 1, 275 mg, 0.75 mmol), Pd (10% wt on active carbon, 27 mg) and MeOH (20 mL) is evacuated to remove air and then the reaction is stirred under a hydrogen balloon until the starting material is consumed. Pd/C is filtered off and the filtrate is concentrated in vacuo to afford Methyl 4-amino-5-methoxy-4'-(methylcarbamoyl)biphenyl-2-carboxylate; ESMS m/z 315.1 (M+H$^+$).

Intermediate 22

4'-Amino-5'-methoxy-N,2'-dimethylbiphenyl-4-carboxamide

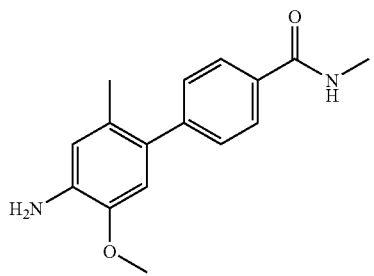 [SMILES: CNC(=O)c1ccc(-c2cc(OC)c(N)cc2C)cc1]

The mixture of 4-chloro-2-methoxy-5-methylaniline (2.0 g, 11.7 mmol), 4-(methylcarbamoyl)phenylboronic acid (2.08 g, 11.7 mmol), 2-dicyclohexylphosphino-2',6'- dimethoxybiphenyl (1.20 g, 2.9 mmol), Pd$_2$(dba)$_3$ (1.1 g, 1.2 mmol), and K$_3$PO$_4$ (7.4 g, 34.9 mmol) in 80 mL of n-butanol is degassed and heated at 130° C. overnight. The reaction mixture is filtered through a pad of celite, and concentrated in vacuo. The crude product mixture is partitioned between EtOAc and brine, the collected organic extracts are dried (Na$_2$SO$_4$), concentrated, and purified by silica gel chromatography (EtOAc/Hexanes:1/4) to afford 4'-Amino-5'-methoxy-N,2'-dimethylbiphenyl-4-carboxamide; ESMS m/z 271.1 (M+H$^+$).

EXAMPLE 1

4'-(5-chloro-4-(5-methyl-1H-pyrazol-3-ylamino)pyrimidin-2-ylamino)-5'-fluoro-N,2'-dimethylbiphenyl-4-carboxamide (1)

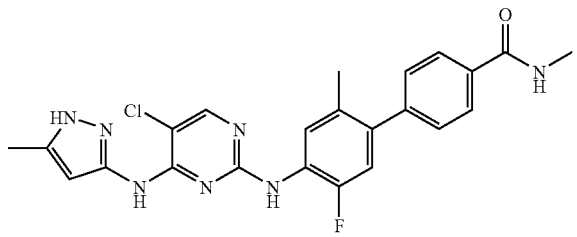

A mixture 2,5-dichloro-N-(5-methyl-1H-pyrazol-3-yl)pyrimidin-4-amine (Intermediate 1, 142 mg, 0.5 mmol) and 4'-amino-5'-fluoro-N,2'-dimethylbiphenyl-4-carboxamide (Intermediate 17, 150 mg, 0.58 mmol) in 2-propanol is treated with conc. aqueous HCl (6 drops). The mixture is sealed and heated in a microwave at 140° C. for 20 min. The mixture is concentrated, and the residue is purified with preparative RP-HPLC to afford the title compound 4'-(5-chloro-4-(5-methyl-1H-pyrazol-3-ylamino)pyrimidin-2-ylamino)-5'-fluoro-N,2'-dimethylbiphenyl-4-carboxamide as white solid. $^1$H NMR (400 MHz, DMSO-d6) δ 9.31 (br, 1H), 9.23 (br, 2H), 8.50 (m, 1H), 8.16 (s, 1H), 7.90 (d, 2H), 7.77 (m, 1H), 7.46 (d, 2H), 7.14 (d, 1H), 6.19 (s, 1H), 2.82 (d, 3H), 2.19 (s, 3H), 2.15 (s, 3H); ESMS m/z 466.1 (M+H$^+$).

EXAMPLE 2

5'-Methoxy-N,2'-dimethyl-4'-(4-(5-methyl-1H-pyrazol-3-ylamino)-5-(trifluoromethyl)pyrimidin-2-ylamino)biphenyl-4-carboxamide (2)

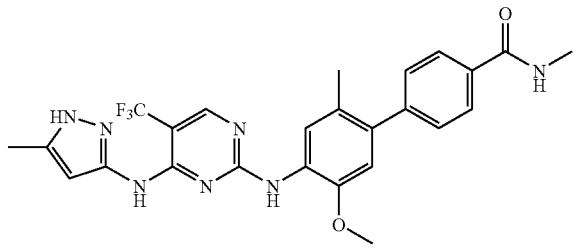

Step 1: 4'-(4-Chloro-5-(trifluoromethyl)pyrimidin-2-ylamino)-5'-methoxy-N,2'-dimethylbiphenyl-4-carboxamide To the mixture of 2,4-dichloro-5-(trifluoromethyl)pyrimidine (100 mg, 0.46 mmol) in 0.5 mL of DCE and 0.5 mL of t-BuOH is added zinc chloride (1.0 M in ether, 0.46 mL, 0.46 mmol), and stirred 30 min. 4'-amino-5'-methoxy-N,2'-dimethylbiphenyl-4-carboxamide (111 mg, 0.414 mmol) and triethylamine (46 mg, 0.46 mmol) are added sequentially, and the reaction is stirred at room temperature overnight. The precipitate is filtered, washed by MeOH, and dried in vacuo to afford 4'-(4-Chloro-5-(trifluoromethyl)pyrimidin-2-ylamino)-5'-methoxy-N,2'-dimethylbiphenyl-4-carboxamide as a white solid; ESMS m/z 451.1 (M+H$^+$).

Step 2: 5'-Methoxy-N,2'-dimethyl-4'-(4-(5-methyl-1H-pyrazol-3-ylamino)-5-(trifluoromethyl)pyrimidin-2-ylamino)biphenyl-4-carboxamide The mixture of 4'-(4-chloro-5-(trifluoromethyl)pyrimidin-2-ylamino)-5'-methoxy-N,2'-dimethylbiphenyl-4-carboxamide (Step 1, 20 mg, 0.044 mmol), 5-methyl-1H-pyrazol-3-amine (4.3 mg, 0.044 mmol), Xantophos (5.0 mg, 0.009 mmol), palladium acetate (II) (1.0 mg, 0.004 mmol), and cesium carbonate (28.6 mg, 0.088 mmol) in 2.0 mL of THF is heated at 150° C. in a microwave reactor for 25 min. The reaction mixture is filtered, the filtrate is concentrated in vacuo, and purified by preparative RP-HPLC to afford 5'-Methoxy-N,2'-dimethyl-4'-(4-(5-methyl-1H-pyrazol-3-ylamino)-5-(trifluoromethyl)pyrimidin-2-ylamino)biphenyl-4-carboxamide; ESMS m/z 512.2 (M+H$^+$).

EXAMPLE 3

(±)-4'-(5-chloro-4-(2-oxoazepan-3-ylamino)pyrimidin-2-ylamino)-5'-fluoro-N,2'-dimethylbiphenyl-4-carboxamide (42-44)

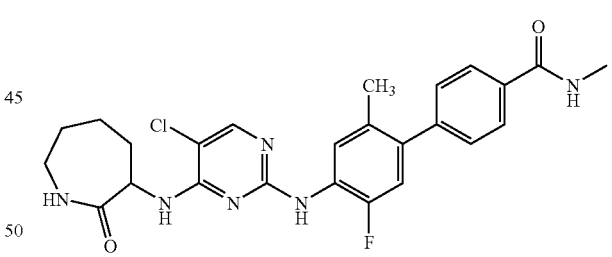

A mixture of 3-(2,5-dichloropyrimidin-4-ylamino)azepan-2-one (Intermediate 16, 28 mg, 0.10 mmol), 4'-Amino-5'-fluoro-N,2'-dimethylbiphenyl-4-carboxamide (Intermediate 17, 31 mg, 0.12 mmol, 1.2 equiv.) and TFA (37 µL, 57 mg, 0.50 mmol, 5 equiv.) in 2-propanol (3 mL) is stirred in a sealed tube at 100° C. for 48 h. The resulting solution is concentrated and then purified by preparative RP-HPLC to afford (±)-4'-(5-chloro-4-(2-oxoazepan-3-ylamino)pyrimidin-2-ylamino)-5'-fluoro-N,2'-dimethylbiphenyl-4-carboxamide; ESMS m/z 497.2 (M+H$^+$).

(±)-4'-(5-chloro-4-(2-oxoazepan-3-ylamino)pyrimidin-2-ylamino)-5'-fluoro-N,2'-dimethylbiphenyl-4-carboxamide is purified into its individual enantiomers via chiral HPLC. The chiral HPLC conditions employed are: 20×250 mm ChiralPak AD column, 80/10/10 hexane/EtOH/MeOH, room temperature, 20 mL/min flow rate, monitor 310 nM, 30 minute run time. Identification of the absolute configuration of the long versus short retention time enantiomer is accomplished by means of repeating the synthetic sequence of Intermediate 16 and Example 3 using optically pure α-amino-ε-caprolactam starting material and co-injecting the final optically pure product with racemic Example 3 onto Chiral HPLC. The (S) enantiomer is the long retention time enantiomer under these conditions, with a retention time of ~19.2 minutes. The (R) enantiomer is the short retention time enantiomer under these conditions, with a retention time of ~12.71 minutes. Concentration of the long and short retention time peaks affords the (S) and (R) enantiomers, respectively.

By repeating the procedures described in examples above, using appropriate starting materials, the following compounds identified in Table 1, are obtained

TABLE 1

| | STRUCTURE | NMR or ESMS |
|---|---|---|
| 1 | 4'-(5-chloro-4-(5-methyl-1H-pyrazol-3-ylamino)pyrimidin-2-ylamino)-5'-fluoro-N,2'-dimethylbiphenyl-4-carboxamide | $^1$H NMR (400 MHz, DMSO-d6) δ 9.31(br, 1H), 9.23(br, 2H), 8.50(m, 1H), 8.16(s, 1H), 7.90 (d, 2H), 7.77(m, 1H), 7.46(d, 2H), 7.14(d, 1H), 6.19(s, 1H), 2.82(d, 3H), 2.19(s, 3H), 2.15 (s, 3H); ESMS m/z 466.1 (M + H$^+$). |
| 2 | 5'-Methoxy-N,2'-dimethyl-4'-(4-(5-methyl-1H-pyrazol-3-ylamino)-5-(trifluoromethyl)pyrimidin-2-ylamino)biphenyl-4-carboxamide | ESMS m/z 512.2 (M + H)$^+$ |
| 3 | 4'-(5-chloro-4-(5-methyl-1H-pyrazol-3-ylamino)pyrimidin-2-ylamino)-5'-methoxy-N,2'-dimethylbiphenyl-3-carboxamide | $^1$H NMR (400 MHz, DMSO-d6) δ 9.48(br, 1H), 8.60(br, 1H), 8.50(m, 1H), 8.20(s, 1H0, 7.88 (m, 1H), 7.80(m, 2H), 7.51(m, 2H), 6.91(s, 1H), 6.20(s, 1H), 3.85(s, 3H), 2.80(d, 3H), 2.19 (s, 3H), 2.12(s, 3H); ESMS m/z 478.2(M + H+). |

TABLE 1-continued

| | STRUCTURE | NMR or ESMS |
|---|---|---|
| 4 | 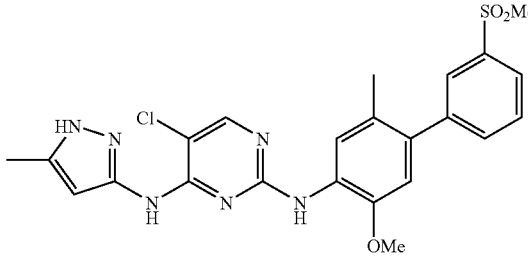

5-chloro-N2-(5-methoxy-2-methyl-3'-(methylsulfonyl)biphenyl-4-yl)-N4-(5-methyl-1H-pyrazol-3-yl)pyrimidine-2,4-diamine | ESMS m/z 499.1 (M + H+). |
| 5 | 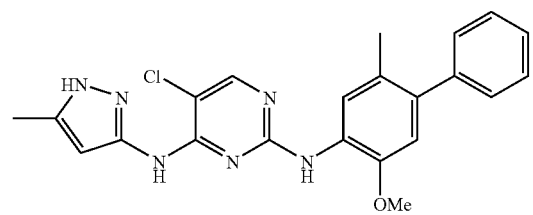

5-chloro-N2-(5-methoxy-2-methylbiphenyl-4-yl)-N4-(5-methyl-1H-pyrazol-3-yl)pyrimidine-2,4-diamine | ESMS m/z 421.1 (M + H+). |
| 6 | 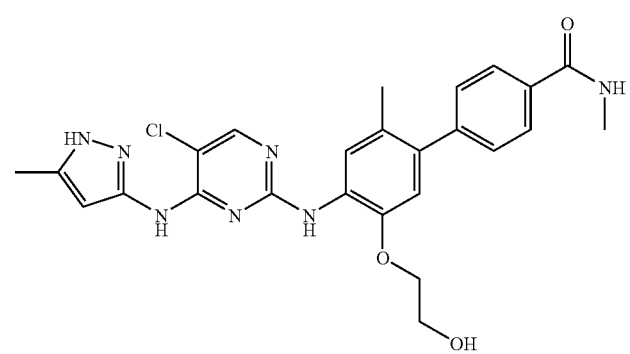

4'-(5-chloro-4-(5-methyl-1H-pyrazol-3-ylamino)pyrimidin-2-ylamino)-5'-(2-hydroxyethoxy)-N,2'-dimethylbiphenyl-4-carboxamide | $^1$H NMR (400 MHz, DMSO-d6) δ 9.23(br, 1H0, 8.56(br, 1H), 8.17(s, 1H), 7.97(s, 1H), 7.88 (d, 2H), 7.44(d, 2H), 6.88(s, 1H), 6.25(s, 1H), 4.05(m, 2H), 371(m, 2H), 2.81(d, 3H), 2.20 (s, 3H), 2.12(s, 3H); ESMS m/z 508.2 (M + H+). |
| 7 | 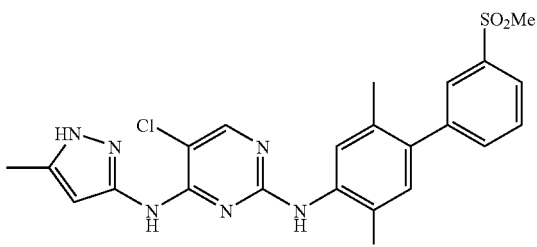

5-chloro-N2-(5-fluoro-2-methyl-3'-(methylsulfonyl)biphenyl-4-yl)-N4-(5-methyl-1H-pyrazol-3-yl)pyrimidine-2,4-diamine | ESMS m/z 487.1 (M + H+). |

TABLE 1-continued

| | STRUCTURE | NMR or ESMS |
|---|---|---|
| 8 | 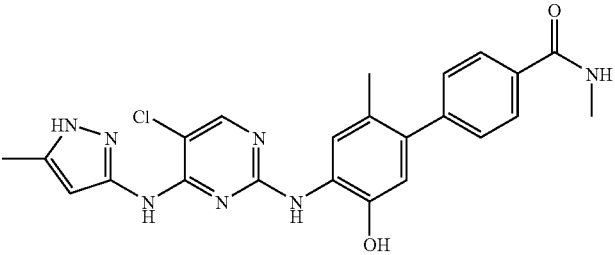<br>4'-(5-chloro-4-(5-methyl-1H-pyrazol-3-ylamino)pyrimidin-2-ylamino)-5'-hydroxy-N,2'-dimethylbiphenyl-4-carboxamide | ESMS m/z 464.1 (M + H+). |
| 9 | 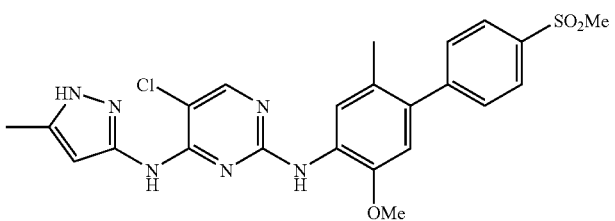<br>5-chloro-N2-(5-methoxy-2-methyl-4'-(methylsulfonyl)biphenyl-4-yl)-N4-(5-methyl-1H-pyrazol-3-yl)pyrimidine-2,4-diamine | ESMS m/z 499.1 (M + H+). |
| 10 | 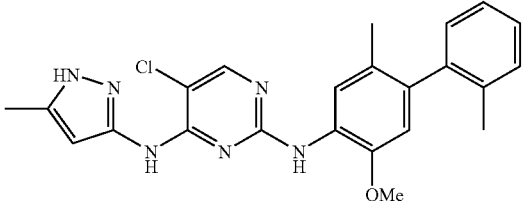<br>5-chloro-N2-(5-methoxy-2,2'-dimethylbiphenyl-4-yl)-N4-(5-methyl-1H-pyrazol-3-yl)pyrimidine-2,4-diamine | ESMS m/z 435.1 (M + H+). |
| 11 | 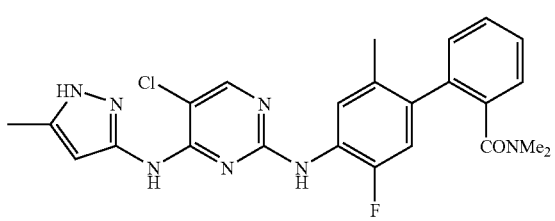<br>4'-(5-chloro-4-(5-methyl-1H-pyrazol-3-ylamino)pyrimidin-2-ylamino)-5'-fluoro-N,N,2'-trimethylbiphenyl-2-carboxamide | ESMS m/z 480.2 (M + H+). |

TABLE 1-continued

| | STRUCTURE | NMR or ESMS |
|---|---|---|
| 12 | 4'-(5-chloro-4-(5-methyl-1H-pyrazol-3-ylamino)pyrimidin-2-ylamino)-5'-fluoro-N-methyl-2'-(trifluoromethyl)biphenyl-4-carboxamide | ESMS m/z 520.1 (M + H+). |
| 13 | 4'-(5-chloro-4-(5-methyl-1H-pyrazol-3-ylamino)pyrimidin-2-ylamino)-5'-fluoro-N,N,2'-trimethylbiphenyl-4-carboxamide | ESMS m/z 480.2 (M + H+). |
| 14 | 4'-(5-chloro-4-(5-methyl-1H-pyrazol-3-ylamino)pyrimidin-2-ylamino)-5'-fluoro-N,N,2'-trimethylbiphenyl-3-carboxamide | ESMS m/z 480.2 (M + H+). |
| 15 | 4'-(5-chloro-4-(5-methyl-1H-pyrazol-3-ylamino)pyrimidin-2-ylamino)-5'-fluoro-2'-methylbiphenyl-4-carboxamide | ESMS m/z 452.1 (M + H+). |

TABLE 1-continued

| | STRUCTURE | NMR or ESMS |
|---|---|---|
| 16 | 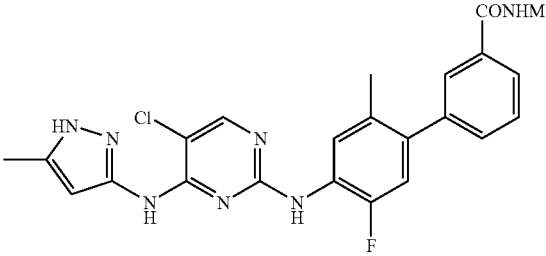<br>4'-(5-chloro-4-(5-methyl-1H-pyrazol-3-ylamino)pyrimidin-2-ylamino)-5'-fluoro-N,2'-dimethylbiphenyl-3-carboxamide | ESMS m/z 465.1 (M + H+). |
| 17 | 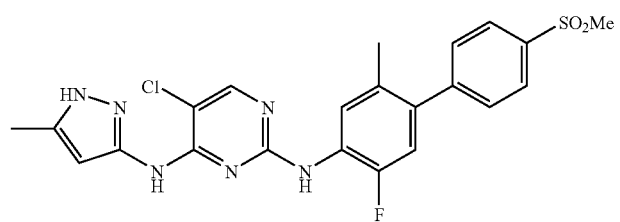<br>5-chloro-N2-(5-fluoro-2-methyl-4'-(methylsulfonyl)biphenyl-4-yl)-N4-(5-methyl-1H-pyrazol-3-yl)pyrimidine-2,4-diamine | ESMS m/z 486.1 (M + H+). |
| 18 | 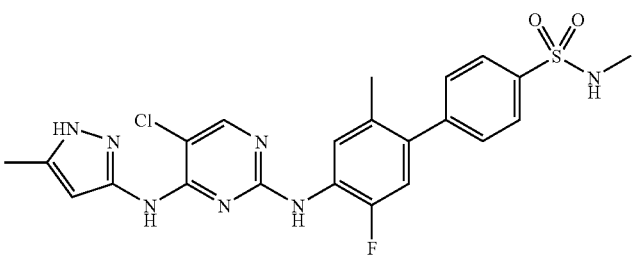<br>4'-(5-chloro-4-(5-methyl-1H-pyrazol-3-ylamino)pyrimidin-2-ylamino)-5'-fluoro-N,2'-dimethylbiphenyl-4-sulfonamide | ESMS m/z 502.1 (M + H+). |
| 19 | 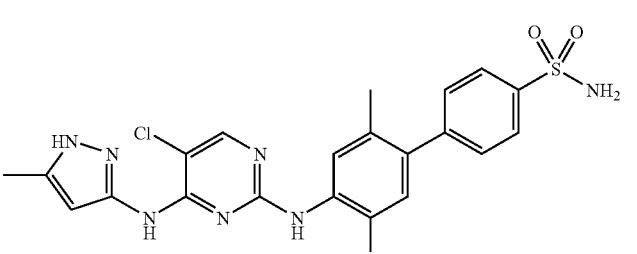<br>4'-(5-chloro-4-(5-methyl-1H-pyrazol-3-ylamino)pyrimidin-2-ylamino)-5'-fluoro-2'-methylbiphenyl-4-sulfonamide | ESMS m/z 488.1 (M + H+). |

TABLE 1-continued

| | STRUCTURE | NMR or ESMS |
|---|---|---|
| 20 | 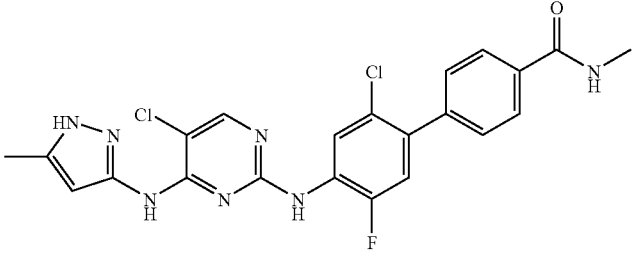<br>2'-chloro-4'-(5-chloro-4-(5-methyl-1H-pyrazol-3-ylamino)pyrimidin-2-ylamino)-5'-fluoro-N-methylbiphenyl-4-carboxamide | ESMS m/z 486.1 (M + H+). |
| 21 | 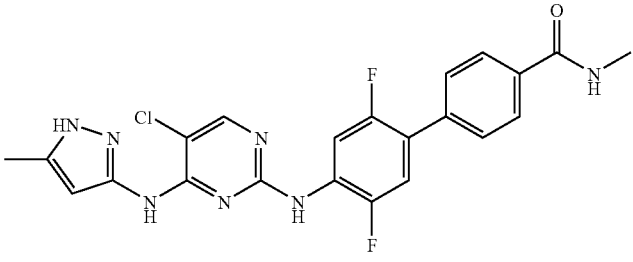<br>4'-(5-chloro-4-(5-methyl-1H-pyrazol-3-ylamino)pyrimidin-2-ylamino)-2',5'-difluoro-N-methylbiphenyl-4-carboxamide | ESMS m/z 470.1 (M + H+). |
| 22 | 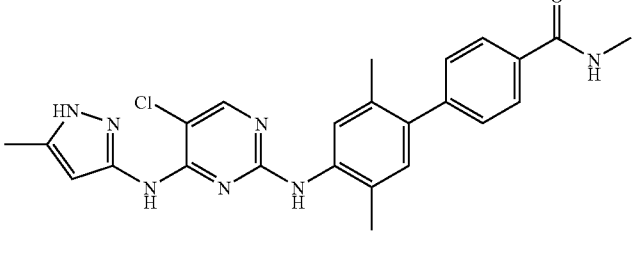<br>4'-(5-chloro-4-(5-methyl-1H-pyrazol-3-ylamino)pyrimidin-2-ylamino)-N,2',5'-trimethylbiphenyl-4-carboxamide | ESMS m/z 462.2 (M + H+). |
| 23 | 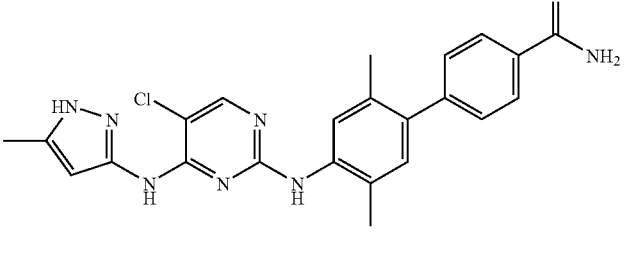<br>4'-(5-chloro-4-(5-methyl-1H-pyrazol-3-ylamino)pyrimidin-2-ylamino)-2',5'-dimethylbiphenyl-4-carboxamide | ESMS m/z 448.2 (M + H+). |

TABLE 1-continued

| | STRUCTURE | NMR or ESMS |
|---|---|---|
| 24 | 4'-(5-chloro-4-(5-methyl-1H-pyrazol-3-ylamino)pyrimidin-2-ylamino)-2'-fluoro-N,5'-dimethylbiphenyl-4-carboxamide | ESMS m/z 466.1 (M + H+). |
| 25 | 4'-(5-chloro-4-(5-methyl-1H-pyrazol-3-ylamino)pyrimidin-2-ylamino)-2'-isopropyl-N,5'-dimethylbiphenyl-4-carboxamide | ESMS m/z 490.2 (M + H+). |
| 26 | 4'-(5-chloro-4-(5-methyl-1H-pyrazol-3-ylamino)pyrimidin-2-ylamino)-N,2',3'-trimethylbiphenyl-4-carboxamide | ESMS m/z 462.2 (M + H+). |
| 27 | 5'-chloro-4'-(5-chloro-4-(5-methyl-1H-pyrazol-3-ylamino)pyrimidin-2-ylamino)-N,2'-dimethylbiphenyl-4-carboxamide | 1H NMR (400 MHz, methanol-d4) δ 8.19(s, 1H), 7.92(d, 2H), 7.79(s, 1H), 7.47(d, 2H), 7.43 (s, 1H), 6.27(s, 1H), 2.96(s, 3H), 2.26(m, 6H); ESMS m/z 482.1 (M + H+). |

TABLE 1-continued

| | STRUCTURE | NMR or ESMS |
|---|---|---|
| 28 | 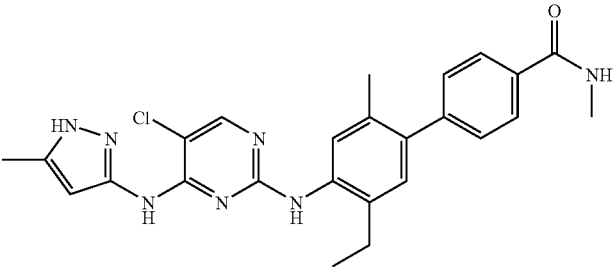<br>4'-(5-chloro-4-(5-methyl-1H-pyrazol-3-ylamino)pyrimidin-2-ylamino)-5'-ethyl-N,2'-dimethylbiphenyl-4-carboxamide | 1H NMR (400 MHz, methanol-d4) δ 8.03(s, 1H), 7.91(d, 2H), 7.47(d, 2H), 7.34(s, 1H), 7.27 (s, 1H), 6.25(br, 1H), 2.96(s, 3H), 2.67(q, 2H0, 2.27(s, 3H), 2.21(s, 3H), 1.20(s, 3H); ESMS m/z 476.2 (M + H+). |
| 29 | 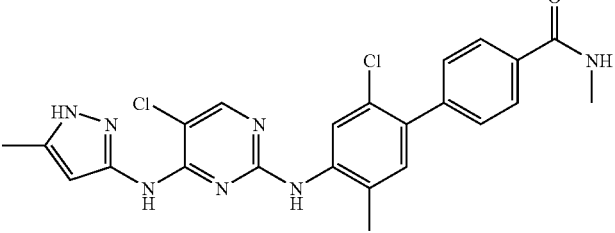<br>2'-chloro-4'-(5-chloro-4-(5-methyl-1H-pyrazol-3-ylamino)pyrimidin-2-ylamino)-N,5'-dimethylbiphenyl-4-carboxamide | ESMS m/z 482.1 (M + H+). |
| 30 | 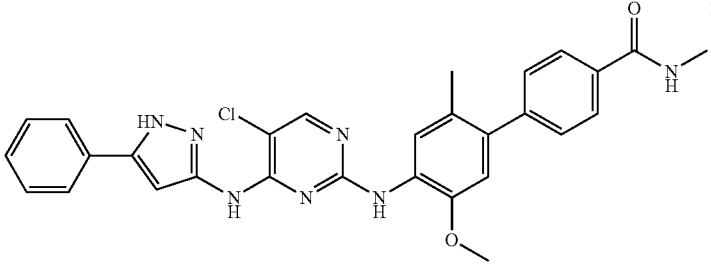<br>4'-(5-chloro-4-(5-phenyl-1H-pyrazol-3-ylamino)pyrimidin-2-ylamino)-5'-methoxy-N,2'-dimethylbiphenyl-4-carboxamide | ESMS m/z 540.2 (M + H+). |
| 31 | 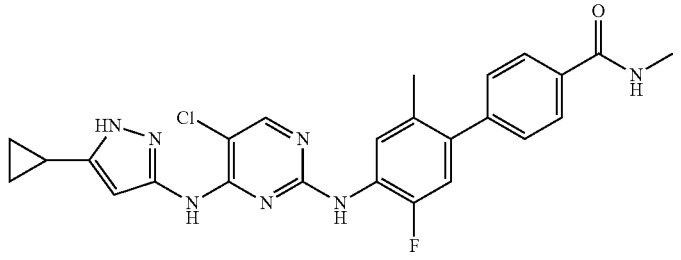<br>4'-(5-chloro-4-(5-cyclopropyl-1H-pyrazol-3-ylamino)pyrimidin-2-ylamino)-5'-fluoro-N,2'-dimethylbiphenyl-4-carboxamide | ESMS m/z 492.2 (M + H+). |

TABLE 1-continued

| | STRUCTURE | NMR or ESMS |
|---|---|---|
| 32 | 4'-(5-chloro-4-(1-methyl-1H-pyrazol-3-ylamino)pyrimidin-2-ylamino)-5'-methoxy-N,2'-dimethylbiphenyl-4-carboxamide | ESMS m/z 478.2 (M + H+). |
| 33 | Ethyl 3-(5-chloro-2-(5-methoxy-2-methyl-4'-(methylcarbamoyl)biphenyl-4-ylamino)pyrimidin-4-ylamino)-1H-pyrazole-4-carboxylate | ESMS m/z 536.2 (M + H+). |
| 34 | N-((4'-(5-chloro-4-(5-methyl-1H-pyrazol-3-ylamino)pyrimidin-2-ylamino)-5'-fluoro-2'-methylbiphenyl-4-yl)methyl)acetamide | ESMS m/z 480.2 (M + H+). |
| 35 | 4-(4-(5-chloro-4-(5-methyl-1H-pyrazol-3-ylamino)pyrimidin-2-ylamino)naphthalen-1-yl)-N-methylbenzamide | ESMS m/z 484.2 (M + H+). |

TABLE 1-continued

| | STRUCTURE | NMR or ESMS |
|---|---|---|
| 36 | 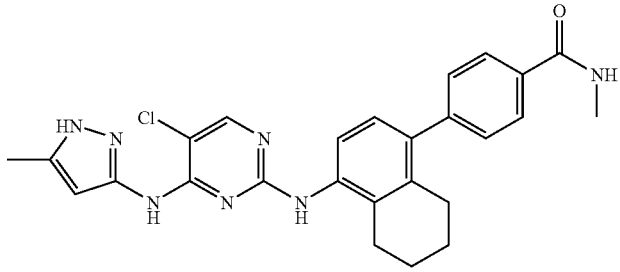\n\n4-(4-(5-chloro-4-(5-methyl-1H-pyrazol-3-ylamino)pyrimidin-2-ylamino)-5,6,7,8-tetrahydronaphthalen-1-yl)-N-methylbenzamide | 1H NMR (400 MHz, Acetone-d6) δ 9.3(br, 1H0, 8.61(br, 2H), 8.03(s, 1H), 8.01(d, 1H), 7.83 (s, 2H), 7.61(br 1H), 7.34(d, 2H), 6.69(d, 1H), 6.00(s, 1H), 2.81(d, 3H), 2.70-2.69(m, 2H), 2.53-2.50(m, 2H), 2.03(s, 3H), 1.64-1.61(m, 2H), 1.54-1.51(m, 2H); ESMS m/z 488.2 (M + H+). |
| 37 | 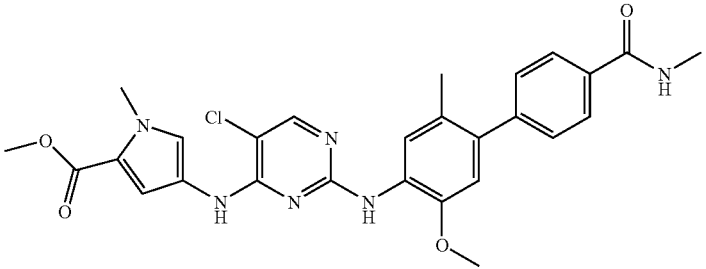\n\nMethyl 4-(5-chloro-2-(5-methoxy-2-methyl-4'-(methylcarbamoyl)biphenyl-4-ylamino)pyrimidin-4-ylamino)-1-methyl-1H-pyrrole-2-carboxylate | ESMS m/z 535.2 (M + H+). |
| 38 | 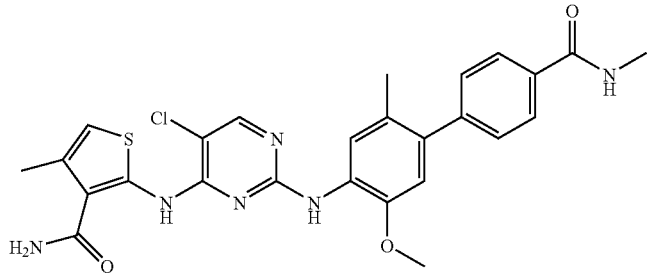\n\n2-(5-Chloro-2-(5-methoxy-2-methyl-4'-(methylcarbamoyl)biphenyl-4-ylamino)pyrimidin-4-ylamino)-4-methylthiophene-3-carboxamide | ESMS m/z 537.1 (M + H+). |
| 39 | 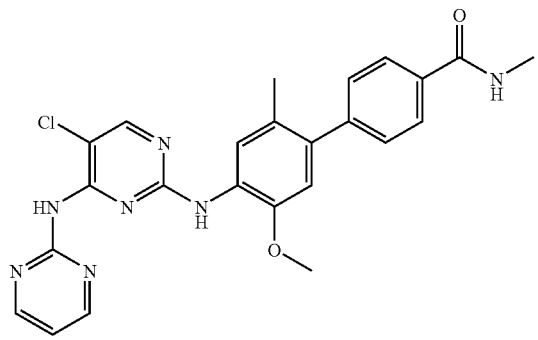\n\n4'-(5-Chloro-4-(pyrimidin-2-ylamino)pyrimidin-2-ylamino)-5'-methoxy-N,2'-dimethylbiphenyl-4-carboxamide | ESMS m/z 476.2 (M + H+). |

TABLE 1-continued

| | STRUCTURE | NMR or ESMS |
|---|---|---|
| 40 | 4'-(5-Chloro-4-(isoxazol-3-ylamino)pyrimidin-2-ylamino)-5'-methoxy-N,2'-dimethylbiphenyl-4-carboxamide | ESMS m/z 465.1 (M + H+). |
| 41 | 4'-(5-Chloro-4-(4,6-dimethylpyridin-2-ylamino)pyrimidin-2-ylamino)-5'-methoxy-N,2'-dimethylbiphenyl-4-carboxamide | ESMS m/z 503.2 (M + H+). |
| 42 | 4'-(5-chloro-4-(2-oxoazepan-3-ylamino)pyrimidin-2-ylamino)-5'-fluoro-N,2'-dimethylbiphenyl-4-carboxamide | ESMS m/z 497.2 (M + H⁺) |
| 43 | (S)-4'-(5-chloro-4-(2-oxoazepan-3-ylamino)pyrimidin-2-ylamino)-5'-fluoro-N,2'-dimethylbiphenyl-4-carboxamide | ESMS m/z 497.2 (M + H⁺) |

TABLE 1-continued

| STRUCTURE | NMR or ESMS |
|---|---|
| 44 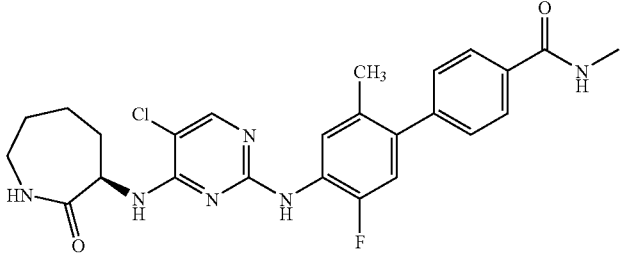 [SMILES: CNC(=O)c1ccc(-c2cc(F)c(Nc3ncc(Cl)c(NC4CCCCNC4=O)n3)cc2C)cc1]<br>(R)-4'-(5-chloro-4-(2-oxoazepan-3-ylamino)pyrimidin-2-ylamino)-5'-fluoro-N,2'-dimethylbiphenyl-4-carboxamide | ESMS m/z 497.2 (M + H$^+$) |
| 45 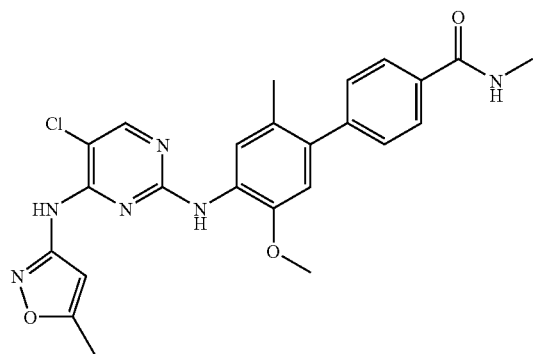<br>4'-(5-Chloro-4-(5-methylisoxazol-3-ylamino)pyrimidin-2-ylamino)-5'-methoxy-N,2'-dimethylbiphenyl-4-carboxamide | ESMS m/z 479.2 (M + H+). |
| 46 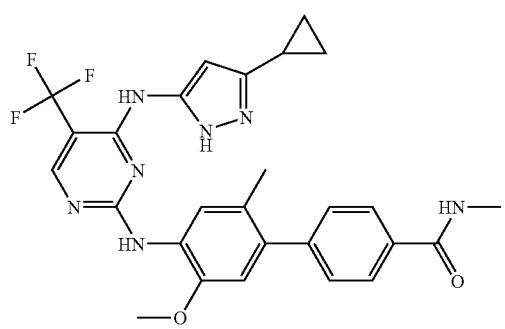<br>4'-(4-(3-cyclopropyl-1H-pyrazol-5-ylamino)-5-(trifluoromethyl)pyrimidin-2-ylamino)-5'-methoxy-N,2'-dimethylbiphenyl-4-carboxamide | ESMS m/z 538.2 (M + H$^+$). |

TABLE 1-continued

| | STRUCTURE | NMR or ESMS |
|---|---|---|
| 47 | 4'-(5-chloro-4-(4-ethylpyridin-2-ylamino)pyrimidin-2-ylmaino)-5'-methoxy-N,2'-dimethylbiphenyl-4-carboxamide | ESMS m/z 503.2 (M + H⁺). |
| 48 | 4'-(5-chloro-4-(4-methylpyridin-2-ylamino)pyrimidin-2-ylamino)-5'-methoxy-N,2'-dimethylbiphenyl-4-carboxamide | ESMS m/z 489.2 (M + H⁺). |
| 49 | 4'-(5-chloro-4-(3-cyclopropyl-1H-pyrazol-5-ylamino)pyrimidin-2-ylamino)-5'-fluoro-2'-methylbiphenyl-4-carboxamide | ESMS m/z 478.1 (M + H⁺). |
| 50 | 4'-(5-chloro-4-(5-methyl-1H-pyrazol-3-ylamino)pyrimidin-2-ylamino)-5'-methoxy-N,2'-dimethylbiphenyl-4-carboxamide | ESMS m/z 478.2 (M + H⁺). |

TABLE 1-continued

| | STRUCTURE | NMR or ESMS |
|---|---|---|
| 51 | 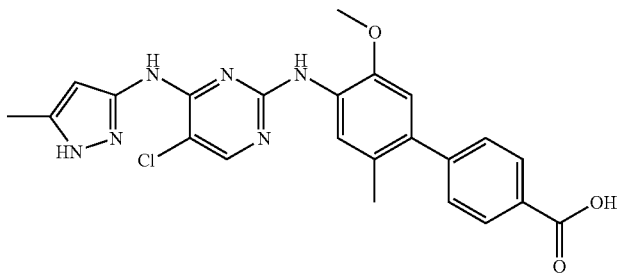<br>4'-(5-chloro-4-(5-methyl-1H-pyrazol-3-ylamino)pyrimidin-2-ylamino)-5'-methoxy-2'-methylbiphenyl-4-carboxylic acid | ESMS m/z 465.1 (M + H$^+$). |
| 52 | 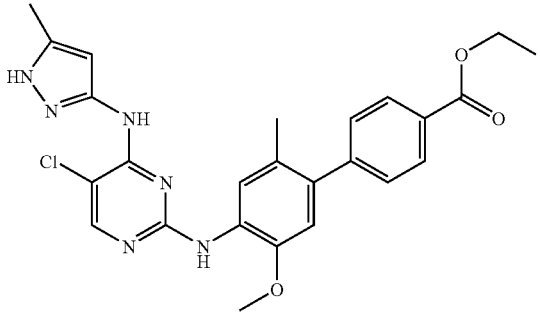<br>ethyl 4'-(5-chloro-4-(5-methyl-1H-pyrazol-3-ylamino)pyrimidin-2-ylamino)-5'-methoxy-2'-methylbiphenyl-4-carboxylate | ESMS m/z 493.2 (M + H$^+$). |
| 53 | 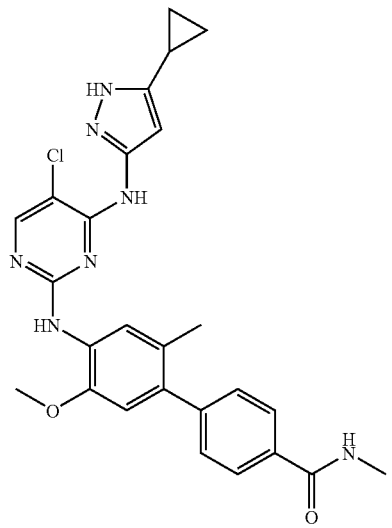<br>4'-(5-chloro-4-(5-cyclopropyl-1H-pyrazol-3-ylamino)pyrimidin-2-ylamino)-5'-methoxy-N,2'-dimethylbiphenyl-4-carboxamide | ESMS m/z 504.2 (M + H$^+$). |

| | STRUCTURE | NMR or ESMS |
|---|---|---|
| 54 | 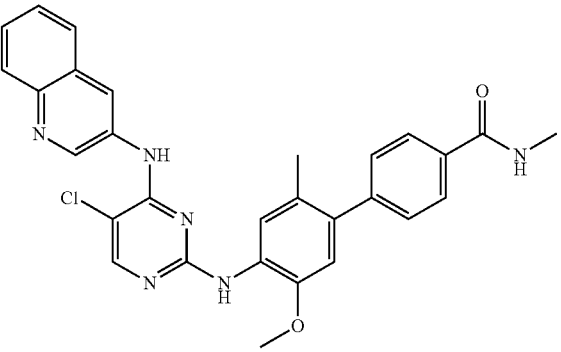<br>4'-(5-chloro-4-(quinolin-3-ylamino)pyrimidin-2-ylamino)-5'-methoxy-N,2'-dimethylbiphenyl-4-carboxamide | ESMS m/z 525.2 (M + H$^+$). |
| 55 | 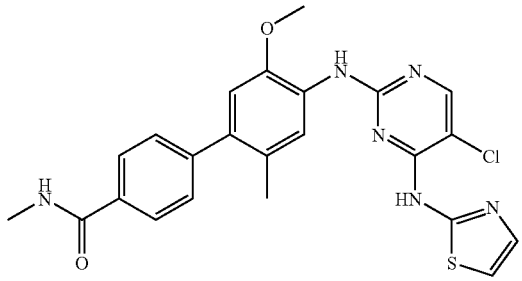<br>4'-(5-chloro-4-(thiazol-2-ylamino)pyrimidin-2-ylamino)-5'-methoxy-N,2'-dimethylbiphenyl-4-carboxamide | ESMS m/z 481.1 (M + H$^+$). |
| 56 | 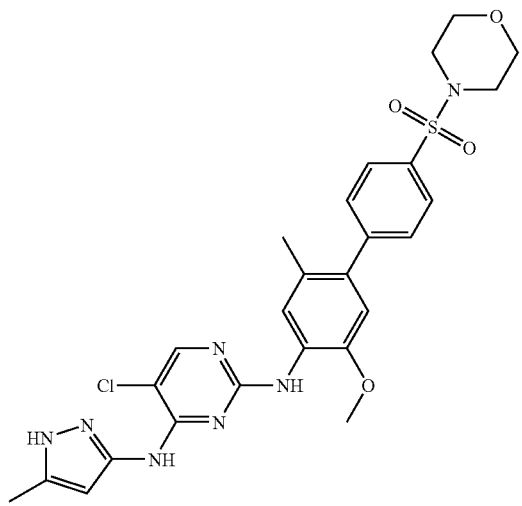<br>5-chloro-N2-(5-methoxy-2-methyl-4'-(morpholinosulfonyl)biphenyl-4-yl)-N4-(5-methyl-1H-pyrazol-3-yl)pyrimidine-2,4-diamine | ESMS m/z 570.2 (M + H$^+$). |

TABLE 1-continued

| | STRUCTURE | NMR or ESMS |
|---|---|---|
| 57 | 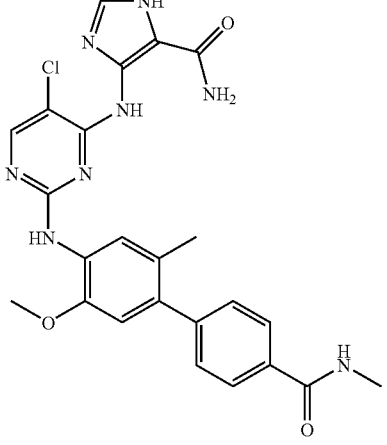<br>4-(5-chloro-2-(5-methoxy-2-methyl-4'-(methylcarbamoyl)biphenyl-4-ylamino)pyrimidin-4-ylamino)-1H-imidazole-5-carboxamide | ESMS m/z 507.2 (M + H$^+$). |
| 58 | 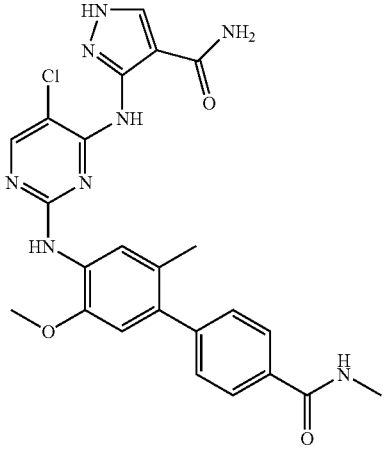<br>3-(5-chloro-2-(5-methoxy-2-methyl-4'-(methylcarbamoyl)biphenyl-4-ylamino)pyrimidin-4-ylamino)-1H-pyrazole-4-carboxamide | ESMS m/z 507.2 (M + H$^+$). |
| 59 | 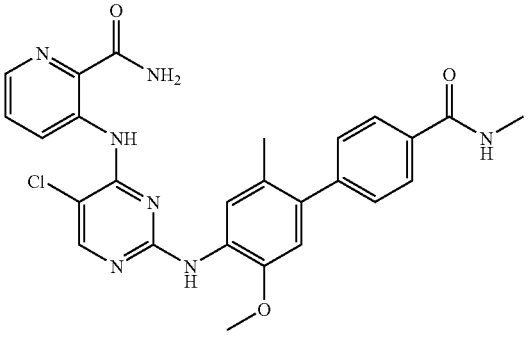<br>3-(5-chloro-2-(5-methoxy-2-methyl-4'-(methylcarbamoyl)biphenyl-4-ylamino)pyrimidin-4-ylamino)picolinamide | ESMS m/z 518.2 (M + H$^+$). |

TABLE 1-continued

| | STRUCTURE | NMR or ESMS |
|---|---|---|
| 60 | 4'-(5-chloro-4-(3-methylisoxazol-5-ylamino)pyrimidin-2-ylamino)-5'-fluoro-N,2'-dimethylbiphenyl-4-carboxamide | ESMS m/z 467.1 (M + H⁺). |
| 61 | 4'-(5-chloro-4-(N-(quinolin-3-yl)acetamido)pyrimidin-2-ylamino)-5'-fluoro-N,2'-dimethylbiphenyl-4-carboxamide | ESMS m/z 555.2 (M + H⁺). |
| 62 | 4'-(4-(1H-indazol-3-ylamino)-5-chloropyrimidin-2-ylamino)-5'-fluoro-N,2'-dimethylbiphenyl-4-carboxamide | ESMS m/z 502.1 (M + H⁺). |
| 63 | 5'-methoxy-N,2'-dimethyl-4'-(4-(5-methyl-1H-pyrazol-3-ylamino)-5-nitropyrimidin-2-ylamino)biphenyl-4-carboxamide | ESMS m/z 489.2 (M + H⁺). |

TABLE 1-continued

| STRUCTURE | NMR or ESMS |
|---|---|
| 64 5′-methoxy-N,2′-dimethyl-4′-(5-methyl-4-(5-methyl-1H-pyrazol-3-ylamino)pyrimidin-2-ylamino)biphenyl-4-carboxamide | ESMS m/z 458.2 (M + H⁺). |
| 65 4′-(5-chloro-4-(5-methyl-1H-pyrazol-3-ylamino)pyrimidin-2-ylamino)-5′-methoxy-N,N,2′-trimethylbiphenyl-3-carboxamide | ESMS m/z 492.2 (M + H⁺). |
| 66 methyl 4′-(5-chloro-4-(5-methyl-1H-pyrazol-3-ylamino)pyrimidin-2-ylamino)-5′-methoxy-2′-methylbiphenyl-4-carboxylate | ESMS m/z 479.2 (M + H⁺). |

TABLE 1-continued

| | STRUCTURE | NMR or ESMS |
|---|---|---|
| 67 | 4'-(5-chloro-4-(5-methyl-1H-pyrazol-3-ylamino)pyrimidin-2-ylamino)-5'-isobutoxy-N,2'-dimethylbiphenyl-4-carboxamide | ESMS m/z 520.2 (M + H⁺). |
| 68 | 4'-(4-((1R,2S)-2-carbamoylcyclohexylamino)-5-chloropyrimidin-2-ylamino)-5'-fluoro-N,2'-dimethylbiphenyl-4-carboxamide | ESMS m/z 511.2 (M + H⁺). |
| 69 | 4'-(4-((1R,2S)-2-carbamoylcyclohexylamino)-5-chloropyrimidin-2-ylamino)-5'-fluoro-N,2'-dimethylbiphenyl-4-carboxamide | ESMS m/z 511.2 (M + H⁺). |

| STRUCTURE | NMR or ESMS |
|---|---|
| 70 (1R,2S,3R,4S)-3-(5-chloro-2-(5-fluoro-2-methyl-4′-(methylcarbamoyl)biphenyl-4-ylamino)pyrimidin-4-ylamino)bicyclo[2.2.1]hept-5-ene-2-carboxamide | ESMS m/z 521.2 (M + H⁺). |
| 71 4′-(4-amino-5-chloro-6-(5-methyl-1H-pyrazol-3-ylamino)pyrimidin-2-ylamino)-5′−methoxy-N,2′-dimethylbiphenyl-4-carboxamide | |

EXAMPLE 4

4'-(5-chloro-4-(2-(cyclopropylcarbamoyl)phenylamino)pyrimidin-2-ylamino)-5'-methoxy-N,2'-dimethylbiphenyl-4-carboxamide (72)

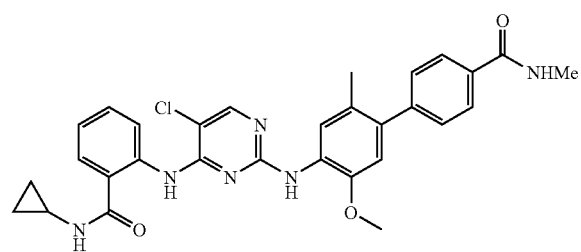 [SMILES: CNC(=O)c1ccc(-c2cc(OC)c(Nc3ncc(Cl)c(Nc4ccccc4C(=O)NC4CC4)n3)cc2C)cc1]

Step 1: Methyl 2-(2,5-dichloropyrimidin-4-ylamino)benzoate

To a solution of 2-(2,5-dichloropyrimidin-4-ylamino)benzoic acid (300 mg, 1.1 mmol) in DCM/MeOH (10/5 mL) is added trimethylsilyl diazomethane in ethyl ether solution (2.0 M, 2 mL). The mixture is stirred for 30 min and concentrated to afford methyl 2-(2,5-dichloropyrimidin-4-ylamino)benzoate as yellow solid.

Step 2: 4'-(5-chloro-4-(2-(cyclopropylcarbamoyl)phenylamino)pyrimidin-2-ylamino)-5'-methoxy-N,2'-dimethylbiphenyl-4-carboxamide A mixture of methyl 2-(2,5-dichloropyrimidin-4-ylamino)benzoate (Step 1, 50 mg, 0.16 mmol) and 4'-amino-5'-methoxy-N,2'-dimethylbiphenyl-4-carboxamide (Intermediate 31, 46 mg, 0.16 mmol) in 2-propanol is treated with conc. aqueous HCl (4 drops). The mixture is sealed and heated in a microwave at 120° C. for 20 min. The mixture is concentrated, and the residue is partitioned between ethyl acetate and sodium carbonate aqueous solution. The organic layer is concentrated to afford crude methyl 2-(5-chloro-2-(5-methoxy-2-methyl-4'-(methylcarbamoyl)biphenyl-4-ylamino)pyrimidin-4-ylamino)benzoate as a brown solid. The obtained crude product is treated with neat cyclopropylamine (0.5 mL). The mixture is heated in a sealed tube at 110° C. overnight. The mixture is concentrated and the residue is applied to RP-HPLC for purification to afford the 4'-(5-chloro-4-(2-(cyclopropylcarbamoyl)phenylamino) pyrimidin-2-ylamino)-5'-methoxy-N,2'-dimethylbiphenyl-4-carboxamide as a white solid. ¹H NMR (400 MHz, CD₃OD) δ 8.75 (m, 1H), 8.49 (m, 1H), 8.15 (s, 1H), 7.91 (d, 2H0, 7.73-7.71 (m, 1H), 7.60 (m, 1H), 7.46 (d, 2H), 7.30-7.26 (m, 1H), 6.98 (s, 1H), 3.88 (s, 3H), 2.96 (s. 3H), 2.90-2.86 (m, 1H), 2.15 (s, 3H), 0.86-0.83 (m, 2H), 0.67-0.65 (m, 2H); ESMS m/z 557.2 (M+H⁺).

EXAMPLE 5

4'-(4-(2-Carbamoylphenylamino)-5-chloropyrimidin-2-ylamino)-5'-methoxy-N-methyl-2'-(pyrrolidine-1-carbonyl)biphenyl-4-carboxamide (73)

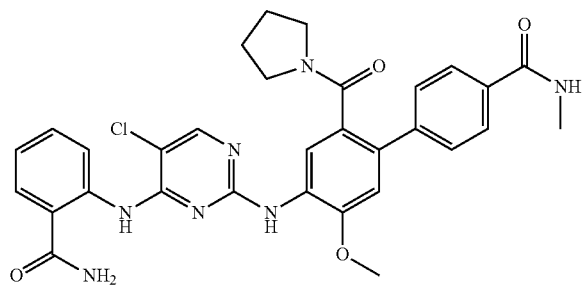 [SMILES: CNC(=O)c1ccc(-c2cc(OC)c(Nc3ncc(Cl)c(Nc4ccccc4C(N)=O)n3)cc2C(=O)N2CCCC2)cc1]

Step 1: Methyl 4-(4-(2-carbamoylphenylamino)-5-chloropyrimidin-2-ylamino)-5-methoxy-4'-(methylcarbamoyl)biphenyl-2-carboxylate.

To the solution of methyl 4-amino-5-methoxy-4'-(methylcarbamoyl)biphenyl-2-carboxylate (Intermediate 27, 117 mg, 0.37 mmol) and 2-(2,5-dichloropyrimidin-4-ylamino)benzamide (Intermediate 3, 316 mg, 1.12 mmol) in 3 mL of i-PrOH is added 5 drops of conc. aqueous HCl. The reaction mixture is heated at 150° C. in a microwave reactor for 30 min, followed by concentration and purification by silica gel chromatography (MeOH/DCM: 1/9) to afford methyl 4-(4-(2-carbamoylphenylamino)-5-chloropyrimidin-2-ylamino)-5-methoxy-4'-(methylcarbamoyl)biphenyl-2-carboxylate; ESMS m/z 561.2 (M+H$^+$).

Step 2: 4'-(4-(2-Carbamoylphenylamino)-5-chloropyrimidin-2-ylamino)-5'-methoxy-N-methyl-2'-(pyrrolidine-1-carbonyl)biphenyl-4-carboxamide The mixture of methyl 4-(4-(2-carbamoylphenylamino)-5-chloropyrimidin-2-ylamino)-5-methoxy-4'-(methylcarbamoyl)biphenyl-2-carboxylate (Step 1, 220 mg, 0.75 mmol) and 1 mL of pyrrolidine is heated at 100° C. overnight. The crude is concentrated in vacuo and applied to preparative RP-HPLC to afford 4'-(4-(2-Carbamoylphenylamino)-5-chloropyrimidin-2-ylamino)-5'-methoxy-N-methyl-2'-(pyrrolidine-1-carbonyl)biphenyl-4-carboxamide; ESMS m/z 600.2 (M+H$^+$).

By repeating the procedures described in examples above, using appropriate starting materials, the following compounds identified in Table 2, are obtained.

TABLE 2

| | STRUCTURE | NMR or ESMS |
|---|---|---|
| 72 | ![structure] 4'-(5-chloro-4-(2-(cyclopropylcarbamoyl)phenylamino)pyrimidin-2-ylamino)-5'-methoxy-N,2'-dimethylbiphenyl-4-carboxamide | $^1$H NMR (400 MHz, CD$_3$OD) δ 8.75(m, 1H), 8.49(m, 1H), 8.15 (s, 1H), 7.91(d, 2h0, 7.73-7.71 (m, 1H), 7.60(m, 1H), 7.46(d, 2H), 7.30-7.26(m, 1H), 6.98(s, 1H), 3.88(s, 3H), 2.96(s, 3H), 2.90-2.86(m, 1H), 2.15(s, 3H), 0.86-0.83(m, 2H), 0.67-0.65(m, 2H); ESMS m/z 557.2 (M + H$^+$). |
| 73 | ![structure] 4'-(3-(2-Carbamoylphenylamino)-4-chlorophenylamino)-5'-methoxy-N-methyl-2'-(pyrrolidine-1-carbonyl)biphenyl-4-carboxamide | ESMS m/z 598.2 (M + H$^+$). |

TABLE 2-continued

| | STRUCTURE | NMR or ESMS |
|---|---|---|
| 74 | 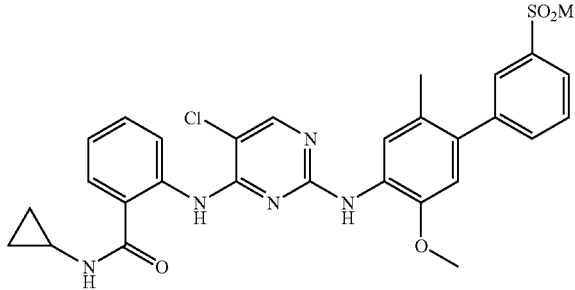<br>2-(5-chloro-2-(5-methoxy-2-methyl-3'-(methylsulfonyl)biphenyl-4-ylamino)pyrimidin-4-ylamino)-N-cyclopropylbenzamide | ESMS m/z 578.2 (M + H⁺) |
| 75 | 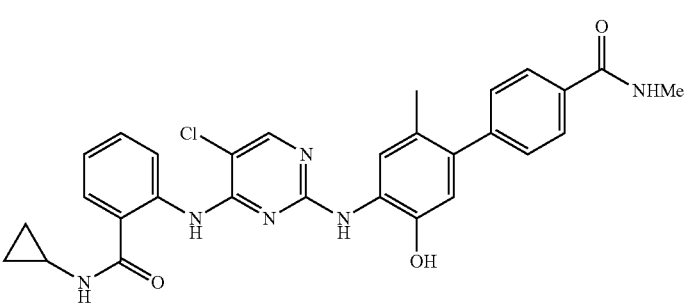<br>4'-(5-chloro-4-(2-(cyclopropylcarbamoyl)phenylamino)pyrimidin-2-ylamino)-5'-hydroxy-N,2'-dimethylbiphenyl-4-carboxamide | ESMS m/z 543.2 (M + H⁺). |
| 76 | 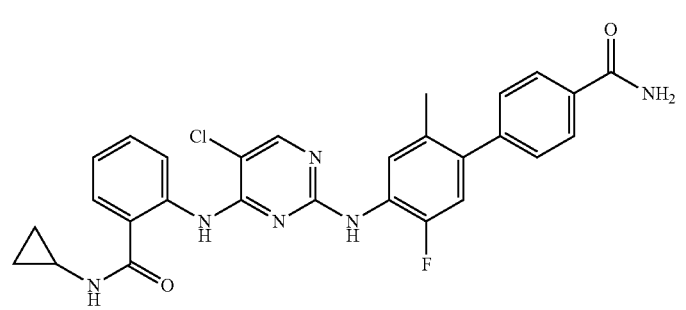<br>4'-(5-chloro-4-(2-(cyclopropylcarbamoyl)phenylamino)pyrimidin-2-ylamino)-5'-fluoro-2'-methylbiphenyl-4-carboxamide | ESMS m/z 531.2 (M + H⁺) |
| 77 | 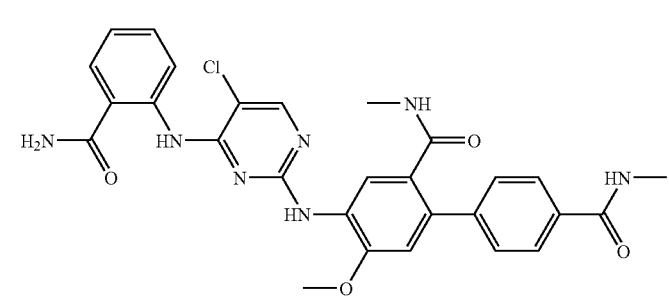<br>4-(4-(2-carbamoylphenylamino)-5-chloropyrimidin-2-ylamino)-5-methoxy-N2,N4'-dimethylbiphenyl-2,4'-dicarboxamide | ESMS m/z 560.2 (M + H⁺). |

TABLE 2-continued

| | STRUCTURE | NMR or ESMS |
|---|---|---|
| 78 | 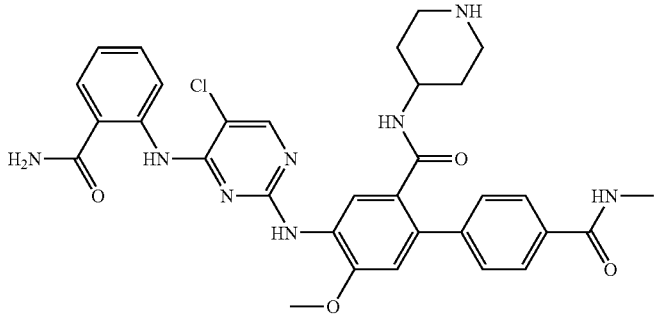<br>4-(4-(2-carbamoylphenylamino)-5-chloropyrimidin-2-ylamino)-5-methoxy-N4'-methyl-N2-(piperidin-4-yl)biphenyl-2,4'-dicarboxamide | ESMS m/z 629.2 (M + H$^+$). |
| 79 | 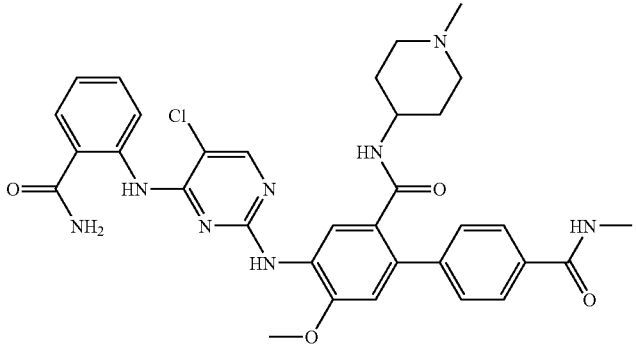<br>4-(4-(2-carbamoylphenylamino)-5-chloropyrimidin-2-ylamino)-5-methoxy-N4'-methyl-N2-(1-methylpiperidin-4-yl)biphenyl-2,4'-dicarboxamide | ESMS m/z 643.2 (M + H$^+$). |
| 80 | 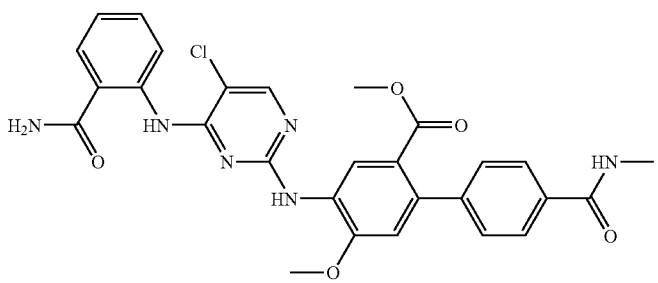<br>methyl 4-(4-(2-carbamoylphenylamino)-5-chloropyrimidin-2-ylamino)-5-methoxy-4'-(methylcarbamoyl)biphenyl-2-carboxylate | ESMS m/z 561.2 (M + H$^+$). |

TABLE 2-continued

| | STRUCTURE | NMR or ESMS |
|---|---|---|
| 81 | 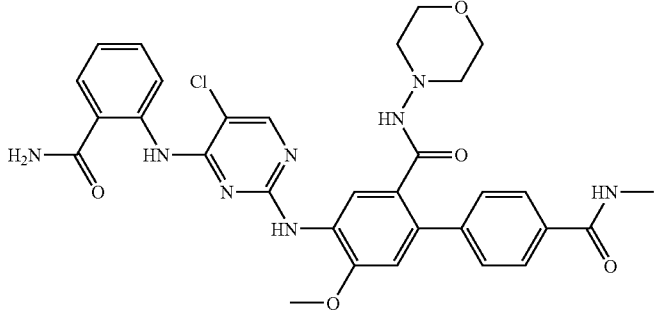<br>4-(4-(2-carbamoylphenylamino)-5-chloropyrimidin-2-ylamino)-5-methoxy-N4'-methyl-N2-morpholinobiphenyl-2,4'-dicarboxamide | ESMS m/z 631.2 (M + H$^+$). |
| 82 | 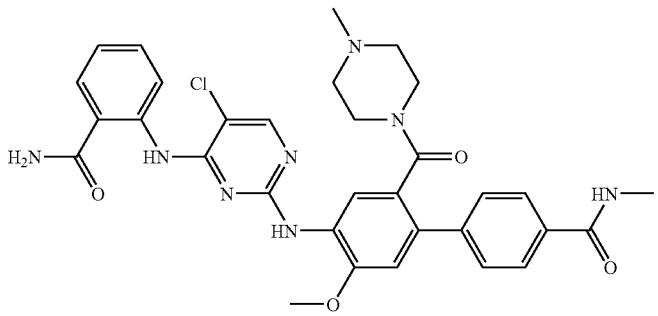<br>4'-(4-(2-carbamoylphenylamino)-5-chloropyrimidin-2-ylamino)-5'-methoxy-N-methyl-2'-(4-methylpiperazine-1-carbonyl)biphenyl-4-carboxamide | ESMS m/z 629.2 (M + H$^+$). |
| 83 | 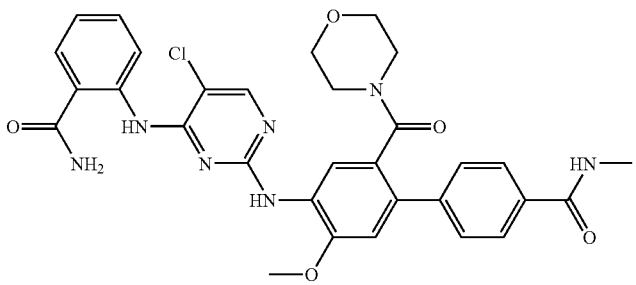<br>4'-(4-(2-carbamoylphenylamino)-5-chloropyrimidin-2-ylamino)-5'-methoxy-N-methyl-2'-(morpholine-4-carbonyl)biphenyl-4-carboxamide | ESMS m/z 616.2 (M + H$^+$). |
| 84 | 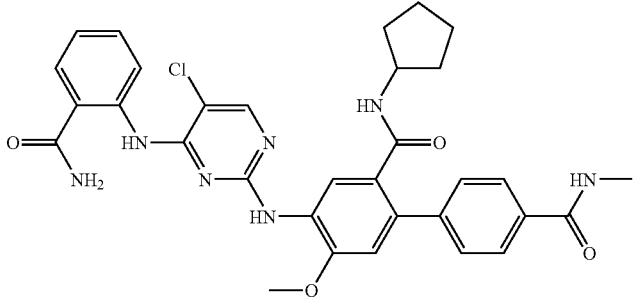<br>4-(4-(2-carbamoylphenylamino)-5-chloropyrimidin-2-ylamino)-N2-cyclopentyl-5-methoxy-N4'-methylbiphenyl-2,4'-dicarboxamide | ESMS m/z 614.2 (M + H$^+$). |

TABLE 2-continued

| | STRUCTURE | NMR or ESMS |
|---|---|---|
| 85 | 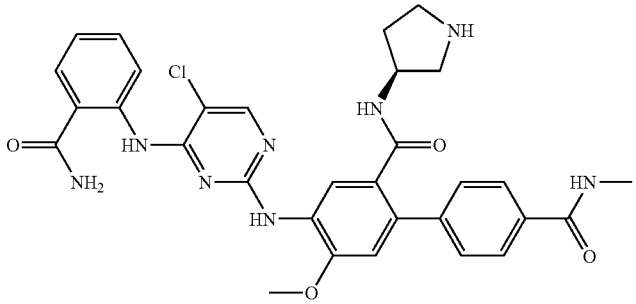<br>(S)-4-(4-(2-carbamoylphenylamino)-5-chloropyrimidin-2-ylamino)-5-methoxy-N4'-methyl-N2-(pyrrolidin-3-yl)biphenyl-2,4'-dicarboxamide | ESMS m/z 615.2 (M + H$^+$). |
| 86 | 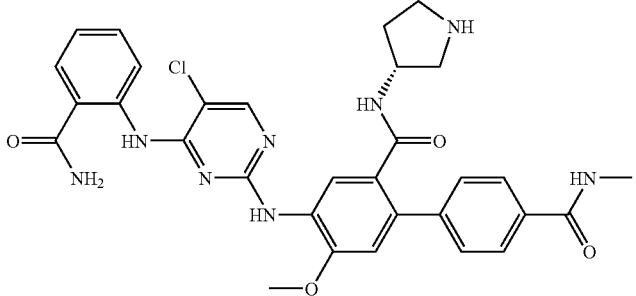<br>(R)-4-(4-(2-carbamoylphenylamino)-5-chloropyrimidin-2-ylamino)-5-methoxy-N4'-methyl-N2-(pyrrolidin-3-yl)biphenyl-2,4'-dicarboxamide | ESMS m/z 615.2 (M + H$^+$). |
| 87 | 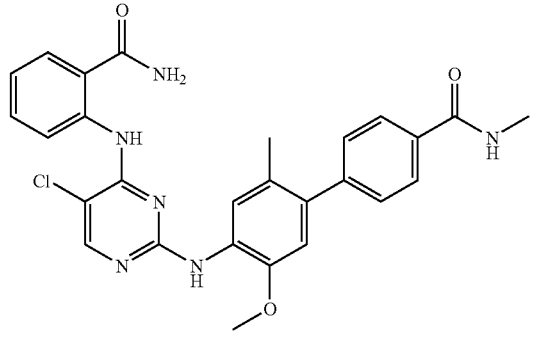<br>4'-(4-(2-carbamoylphenylamino)-5-chloropyrimidin-2-ylamino)-5'-methoxy-N,2'-dimethylbiphenyl-4-carboxamide | ESMS m/z 517.2 (M + H$^+$). |

TABLE 2-continued

| | STRUCTURE | NMR or ESMS |
|---|---|---|
| 88 | 4'-(5-chloro-4-(2-(2-(dimethylamino)ethylcarbamoyl)phenylamino)pyrimidin-2-ylamino)-5'-fluoro-N,2'-dimethylbiphenyl-4-carboxamide | ESMS m/z 576.2 (M + H$^+$). |
| 89 | 4'-(4-(2-(2-aminoethylcarbamoyl)phenylamino)-5-chloropyrimidin-2-ylamino)-5'-fluoro-N,2'-dimethylbiphenyl-4-carboxamide | ESMS m/z 548.2 (M + H$^+$). |
| 90 | 4'-(5-chloro-4-(2-(2-hydroxyethylcarbamoyl)phenylamino)pyrimidin-2-ylamino)-5'-fluoro-N,2'-dimethylbiphenyl-4-carboxamide | ESMS m/z 549.2 (M + H$^+$). |

Assays

The IC$_{50}$ of a drug may be determined constructing a dose-response curve and examining the effect of different concentrations of antagonist on reversing agonist activity. IC$_{50}$ values may be calculated for a given antagonist by determining the concentration needed to inhibit half of the maximum biological response of the agonist. To calculate IC$_{50}$ values, a series of dose-response data (e.g., drug concentrations x1, x2, . . . , xn and growth inhibition y1, y2, . . . , yn, the values of y are in the range of 0-1) is generated. IC$_{50}$ values may be determined by a computer-aided system using the formula:

$$y = D + ((A-D)/(1+10^{(x-\log(IC50)B)})$$

where A is the ratio of growth inhibition between lowest drug concentration and control; B is the slope of sigmoidal curvel; and D is the ratio of growth inhibition between highest drug concentration and control.

The $IC_{50}$ value is given as that concentration of the test compound that results in growth inhibition that is 50% lower than that obtained using the control without inhibitor. The compounds of the invention in free form or in pharmaceutically acceptable salt form may exhibit valuable pharmacological properties, for example, as indicated by the in vitro tests described in this application. In general, compounds of the invention have $IC_{50}$ values from 1 nM to 10 µM. In some examples, compounds of the invention have $IC_{50}$ values from 0.01 µM to 5 µM. In other examples, compounds of the invention have $IC_{50}$ values from 0.01 µM to 1 µM, or more particularly from 1 nM to 1 µM. In yet other examples, compounds of the invention have $IC_{50}$ values of less than 1 nM or more than 10 µM. The compounds of the invention may exhibit a percentage inhibition of greater than 50%, or in other embodiments, may exhibit a percentage inhibition greater than about 70%, against IGF-1R at 10 µM.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each TEL-fusion kinase and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #S V30014.03, Logan, Utah), 4.5 g/L glucose (Sigma #G5400, St. Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 µL/well using a µFill liquid dispenser (BioTek, Winooski, Vt., USA). Duplicate plates are run for each cell line. Test and control compounds are serially diluted with DMSO and arrayed in a polypropylene 384-well plate. 50 mL of compound is transferred into the assay plates using a pin-transfer device, and the plates are incubated at 37° C. (5% $CO_2$) for 48 hours. 25 µL Britelite (Perkin Elmer) is added and luminescence is quantified using Analyst GT (Molecular Devices). Custom curve-fitting software is used to produce a logistic fit of percent cell viability as a function of the logarithm of inhibitor concentration. The $IC_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Enzymatic HTRF Assay

IGF-1R and INSR (insulin receptor) are purchased from Upstate. Following reagents are prepared in-house; 10×kinase buffer (KB) (200 mM Tris (pH 7.0), 100 mM $MgCl_2$, 30 mM $MnCl_2$, 50 nM $NaVO_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GTOBLB), Mab PT66-K, (61T66KLB), Streptavidin-$XL^{ent}$ (611SAXLB)) are purchased from CIS-US, Inc.

The substrate/ATP mix is prepared by adding ATP (final concentration, 3 µM) and biotinylated poly-GT (final concentration, 10 ng/µl) into 1×KB, and dispensed into Proxiplate-384 at 5 µl/well using gill (Bio-TEK). Serially diluted compounds (in DMSO) are transferred into plate using 50 mL pinhead. 5 µL of prepared Enzyme mix (enzyme (final concentration, 5 ng/µl), mixed with BSA and DTT in 1×KB) is added to initiate kinase reaction using gill (Bio-TEK). Assay plate is incubated at room temperature for 2 hours. Detection mix is prepared by adding both Mab PT66-K and Streptavidin-$XL^{ent}$ into 0.5×KB solution containing KF (final concentration, 125 mM), EDTA (final concentration, 50 mM) and BSA (final concentration, 100 µg/ml) in. At the end of reaction, 10 µL of detection mix is added and incubated for 30 minutes at room temperature before measurement. HTRF signal is detected using Analyst-GT (molecular Devices).

Cancer Cell Proliferation Inhibition Assay

For luciferizing cancer cell line, each cell line is transduced by ampholytic retrovirus carrying both luciferase gene and puromycin-resistant gene whose expression is driven by LTR. Briefly, the retroviral vector pMSCV-Puro-Luc is transfected into Phoenix cell line using Fugene6 (Roche) according to manufacturer's instruction. Two days after transfection, supernatant containing virus is harvested and filtered with 0.2 µm filter. Harvested virus is used immediately or stored at −80° C. For infection, cultured cancer cells are harvested and plated ($5 \times 10^5$ cells/well in 1 ml medium) on 6-well tissue culture plate. For each well, 3 ml virus supernatant is added together with 400 µl FBS, 40 µl 1 M HEPES (pH8.0) and 4 µl of polybrene (10 µg/ml, Specialty media). The plate is centrifuged down for 90 minutes at 2500 rpm for spin-infection and is transferred into an incubator for overnight infection. Next day, infected cell line is transferred into T-75 flask containing fresh medium and incubated for one day. Two days after infection, puromycin is added at the final concentration of 1 µg/ml to begin selection. Within 1-2 weeks, puromycin-resistant cell line is established after at least two subsequent splits and is preserved as luciferized stock.

Each cell line is harvested while in log phase growth by trypsinization and diluted in respective media to appropriate density prior to plating. Cells are dispensed using gill (BioTeK) at 50 µl/well into white walled clear bottom plates (Greiner). Cells are then placed in 37° C. incubator supplying 5% CO2 overnight. Compounds are transferred using 50mL/well Pintool technology via Platemate (Matrix). Assay plates are then placed back into the incubator for 3 days. On the third day following compound transfer, BRITELITE® (Perkin Elmer, diluted according to manufacturer's suggestion) is added to assay plates and read on Analyst GT (Molecular Devices) or Envision (Perkin Elmer). Raw data is generated in RLU.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (1):

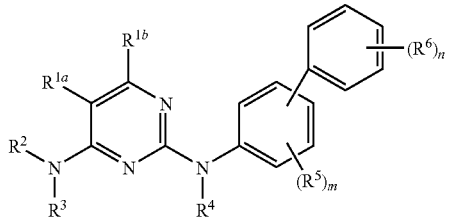

(1)

or a pharmaceutically acceptable salt thereof;
wherein $R^{1a}$ is halo, $C_{1-6}$ alkyl, or a halo-substituted $C_{1-6}$ alkyl;
$R^{1b}$ is H;
$R^2$ is a $C_{6-10}$ carbocyclic, or a 5-10 membered heteroaryl or 5-7 membered heterocyclic ring each having 1-3 heteroatoms selected from N, O and S; each of which is optionally substituted with $C_{1-6}$ alkyl, -L-Y, -L-C(O)O$_{0-1}$—(CR$_2$)$_q$—R$^8$ or -L-C(O)—NRR$^8$;
$R^3$ is H or CO(R$^7$) wherein R$^7$ is $C_{1-6}$ alkyl;
$R^4$ is H;
$R^5$ and $R^6$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^5$ and $R^6$ are independently halo, nitro, cyano, OR$^8$, O(CR$_2$)$_p$—OR$^8$, -L-NR(R$^8$), -L-NR(CR$_2$)$_p$OR$^8$, -L-NR—(CR$_2$)$_q$—C(O)R$^9$, -L-Y, -L-C(O)O$_{0-1}$—(CR$_2$)$_q$—R$^8$, -L-C(O)—NRR$^8$, -L-C(O)—NR—(CR$_2$)$_p$—NRR$^8$, -L-C(O)NR(CR$_2$)$_p$OR$^8$, -L-C(O)—(CR$_2$)$_q$—NR—C(O)—R$^9$, -L-C(O)NR(CR$_2$)$_p$SR$^8$, -L-C(O)NR(CR$_2$)$_p$S(O)$_{1-2}$R$^9$, -L-S(O)$_2$R$^9$, -L-S(O)$_2$NRR$^8$, -L-S(O)$_2$NR(CR$_2$)$_p$NR(R$^8$), -L-S(O)$_2$NR(CR$_2$)$_p$OR$^8$;
alternatively, two adjacent $R^5$ groups together with the carbon atoms they are attached to may form a 9-14 membered ring;
$R^8$ and $R^9$ are independently (CR$_2$)$_9$Y or $C_{1-6}$ alkyl, $C_{1-6}$ alkoxy, $C_{2-6}$ alkenyl or $C_{2-6}$ alkynyl, each of which may be optionally substituted with halo, amino or hydroxyl; or R$^8$ is H;
each R is H or $C_{1-6}$ alkyl;
Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $C_{1-6}$ alkyl;
L is (CR$_2$)$_{1-4}$ or a bond;
m is 2-4;
p is 1-4; and n and q are independently 0-4.

2. The compound of claim 1, wherein said compound is of Formula (2A) or (2B):

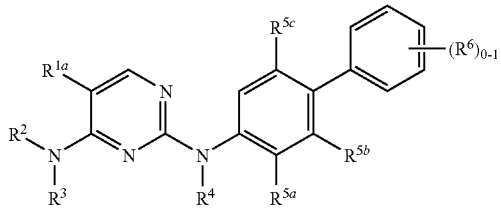

(2A)

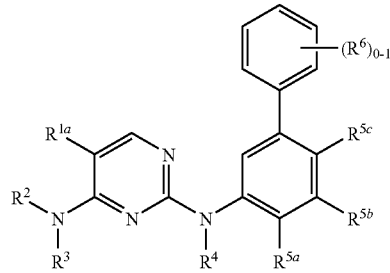

(2B)

wherein one of $R^{5a}$, $R^{5b}$ and $R^{5c}$ is H and the others and R$^6$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{5a}$, $R^{5b}$, $R^{5c}$ and R$^6$ are independently halo, nitro, cyano. OR$^8$, O(CR$_2$)$_p$—OR$^8$, -L-NR(R$^8$), -L-NR(CR$_2$)$_p$OR$^8$, -L-NR-L-C(O)R$^9$, -L-Y, -L-C(O)O$_{0-1}$—(CR$_2$)$_q$—R$^8$, -L-C(O)—NRR$^8$, -L-C(O)—NR—(CR$_2$)$_p$—NRR$^8$, -L-C(O)NR(CR$_2$)$_p$OR$^8$, -L-C(O)—(CR$_2$)$_q$—NR—C(O)—R$^9$, -L-C(O)NR(CR$_2$)$_p$SR$^8$, -L-C(O)NR(CR$_2$)$_p$S(O)$_{1-2}$R$^9$, -L-S(O)$_2$R$^9$, -L-S(O)$_2$NRR$^8$, -L-S(O)$_2$NR(CR$_2$)$_p$NR(R$^8$), -L-S(O)$_2$NR(CR$_2$)$_p$OR$^8$; wherein L is (CR$_2$)$_{1-4}$ or a bond;

$R^8$ and $R^9$ are independently (CR$_2$)$_9$Y or $C_{1-6}$ alkyl, $C_{1-6}$ alkoxy, $C_{2-6}$ alkenyl or $C_{2-6}$ alkynyl, each of which may be optionally substituted with halo, amino or hydroxyl; or R$^8$ is H;

each R is H or $C_{1-6}$ alkyl;

Y is a $C_{3-12}$ carbocyclic ring, $C_{6-10}$ aryl or a 5-10 membered heteroaryl or heterocyclic ring, each having 1-4 heteroatoms selected from N, O and S; wherein Y is optionally substituted with 1-3 $C_{1-6}$ alkyl groups;

p is 1-4; and q is 0-4.

3. The compound of claim 2, wherein $R^{5b}$ is H;

$R^{5a}$ and $R^{5c}$ are independently halo, hydroxyl, $C_{1-6}$ alkyl, $C_{1-6}$ alkoxy, halo-substituted $C_{1-6}$ alkyl or halo-substituted $C_{1-6}$ alkoxy; and $R^6$ is $C_{1-6}$ alkyl, -L-NR-L-C(O)R$^9$, -L-C(O)O$_{0-1}$—(CR$_2$)$_q$—R$^8$, -L-C(O)—NRR$^8$, -L-S(O)$_2$R$^9$ or -L-S(O)$_2$NRR$^8$.

4. The compound of claim 2, wherein $R^{5c}$ is H; and $R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy.

5. The compound of claim 1, wherein $R^2$ is pyrazolyl, pyrrolyl, thiophenyl, pyrimidinyl, isoxazolyl, pyridyl, azepan-2-onyl, thiazolyl, imidazolyl, isoxazolyl, indazolyl, quinolinyl, or bicycle[2.2.1]hept-5-enyl, each of which is optionally substituted with 1-2 R$^6$ groups.

6. The compound of claim 1, wherein said compound is selected from the group consisting of

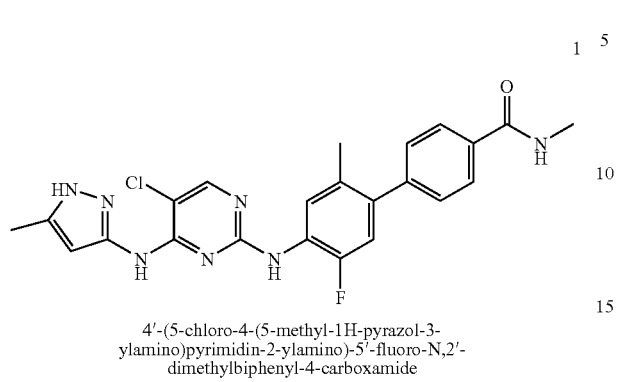

4'-(5-chloro-4-(5-methyl-1H-pyrazol-3-ylamino)pyrimidin-2-ylamino)-5'-fluoro-N,2'-dimethylbiphenyl-4-carboxamide

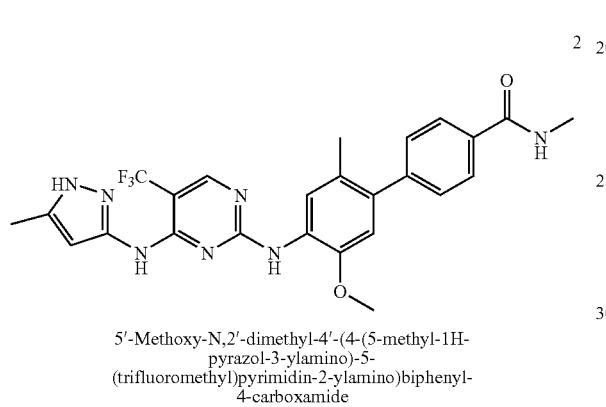

5'-Methoxy-N,2'-dimethyl-4'-(4-(5-methyl-1H-pyrazol-3-ylamino)-5-(trifluoromethyl)pyrimidin-2-ylamino)biphenyl-4-carboxamide

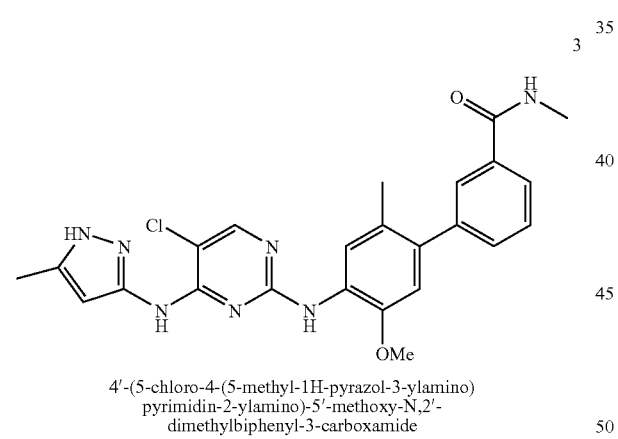

4'-(5-chloro-4-(5-methyl-1H-pyrazol-3-ylamino)pyrimidin-2-ylamino)-5'-methoxy-N,2'-dimethylbiphenyl-3-carboxamide

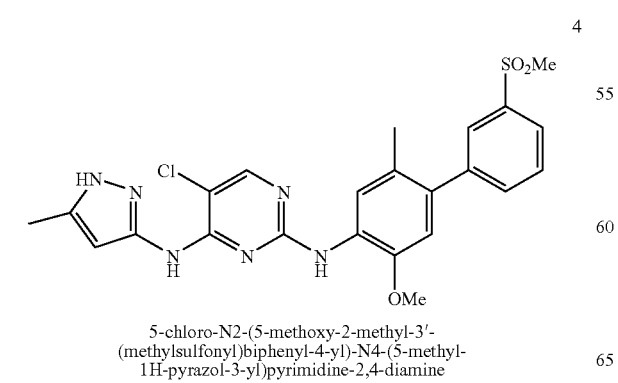

5-chloro-N2-(5-methoxy-2-methyl-3'-(methylsulfonyl)biphenyl-4-yl)-N4-(5-methyl-1H-pyrazol-3-yl)pyrimidine-2,4-diamine

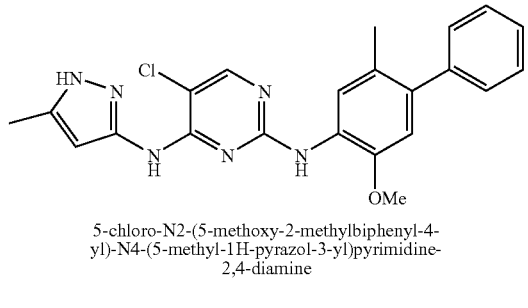

5-chloro-N2-(5-methoxy-2-methylbiphenyl-4-yl)-N4-(5-methyl-1H-pyrazol-3-yl)pyrimidine-2,4-diamine

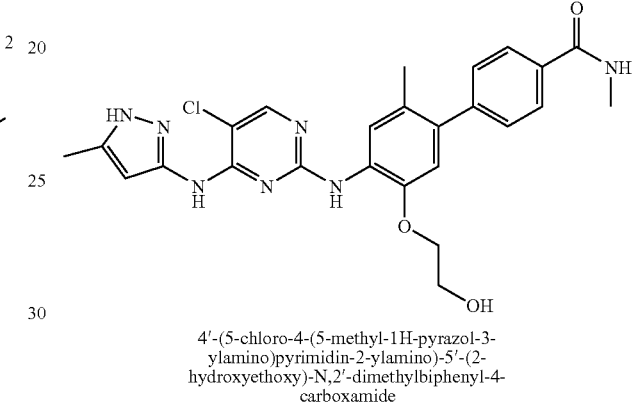

4'-(5-chloro-4-(5-methyl-1H-pyrazol-3-ylamino)pyrimidin-2-ylamino)-5'-(2-hydroxyethoxy)-N,2'-dimethylbiphenyl-4-carboxamide

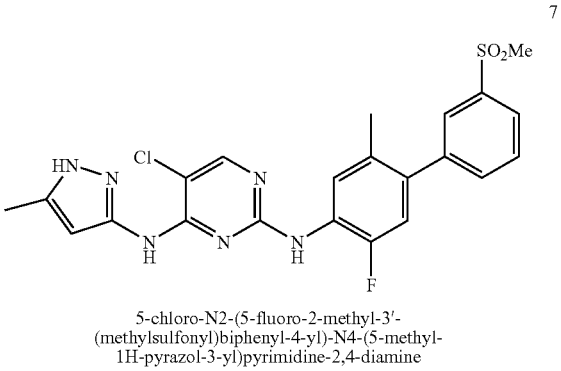

5-chloro-N2-(5-fluoro-2-methyl-3'-(methylsulfonyl)biphenyl-4-yl)-N4-(5-methyl-1H-pyrazol-3-yl)pyrimidine-2,4-diamine

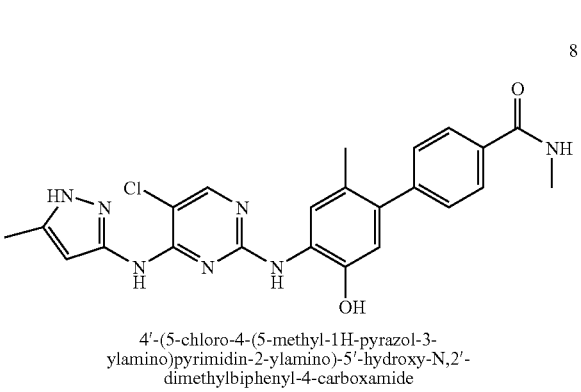

4'-(5-chloro-4-(5-methyl-1H-pyrazol-3-ylamino)pyrimidin-2-ylamino)-5'-hydroxy-N,2'-dimethylbiphenyl-4-carboxamide -continued

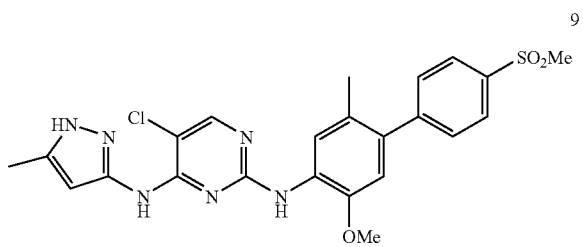

5-chloro-N2-(5-methoxy-2-methyl-4'-
(methylsulfonyl)biphenyl-4-yl)-N4-(5-methyl-
1H-pyrazol-3-yl)pyrimidine-2,4-diamine

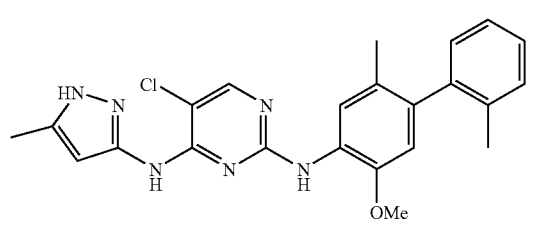

5-chloro-N2-(5-methoxy-2,2'-dimethylbiphenyl-
4-yl)-N4-(5-methyl-1H-pyrazol-3-
yl)pyrimidine-2,4-diamine

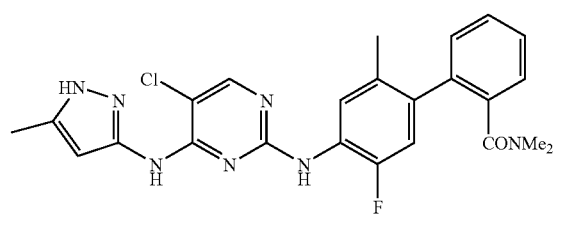

4'-(5-chloro-4-(5-methyl-1H-pyrazol-3-
ylamino)pyrimidin-2-ylamino)-5'-fluoro-N,N,2'-
trimethylbiphenyl-2-carboxamide

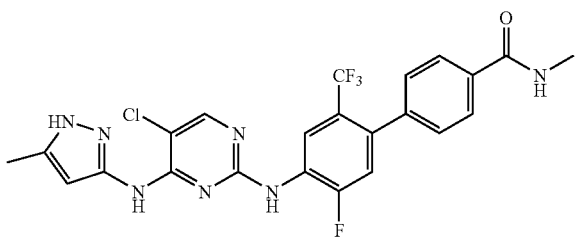

4'-(5-chloro-4-(5-methyl-1H-pyrazol-3-
ylamino)pyrimidin-2-ylamino)-5'-fluoro-N-
methyl-2'-(trifluoromethyl)biphenyl-4-
carboxamide

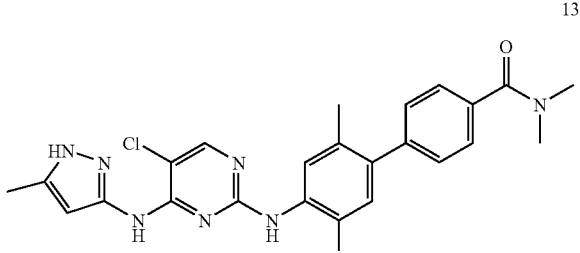

4'-(5-chloro-4-(5-methyl-1H-pyrazol-3-
ylamino)pyrimidin-2-ylamino)-5'-fluoro-N,N,2'-
trimethylbiphenyl-4-carboxamide

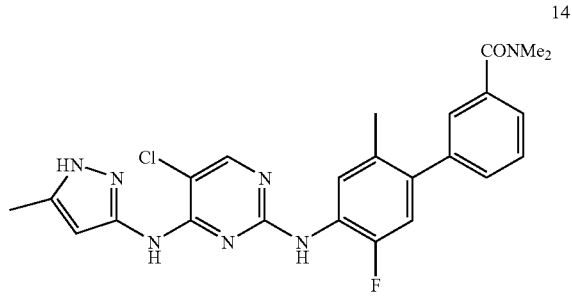

4'-(5-chloro-4-(5-methyl-1H-pyrazol-3-
ylamino)pyrimidin-2-ylamino)-5'-fluoro-N,N,2'-
trimethylbiphenyl-3-carboxamide

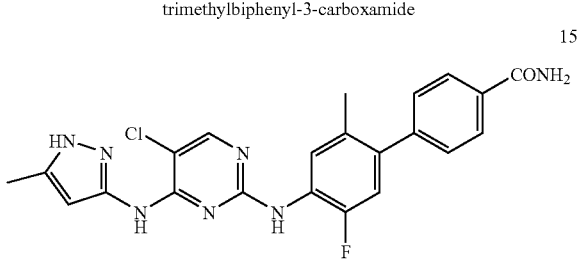

4'-(5-chloro-4-(5-methyl-1H-pyrazol-3-
ylamino)pyrimidin-2-ylamino)-5'-fluoro-2'-
methylbiphenyl-4-carboxamide

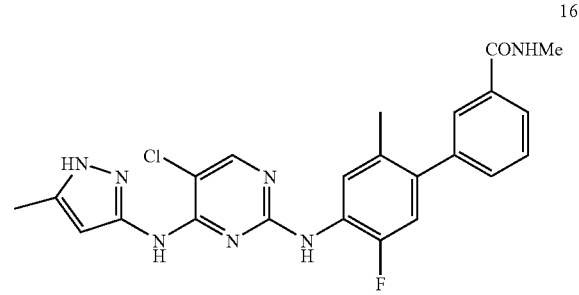

4'-(5-chloro-4-(5-methyl-1H-pyrazol-3-
ylamino)pyrimidin-2-ylamino)-5'-fluoro-N,2'-
dimethylbiphenyl-3-carboxamide

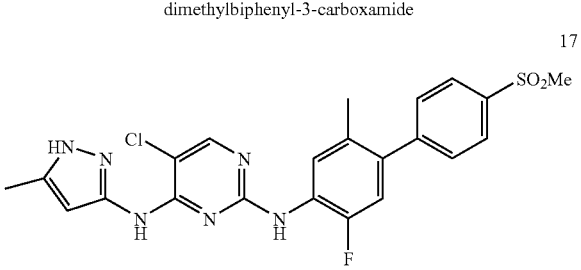

5-chloro-N2-(5-fluoro-2-methyl-4'-
(methylsulfonyl)biphenyl-4-yl)-N4-(5-methyl-
1H-pyrazol-3-yl)pyrimidine-2,4-diamine

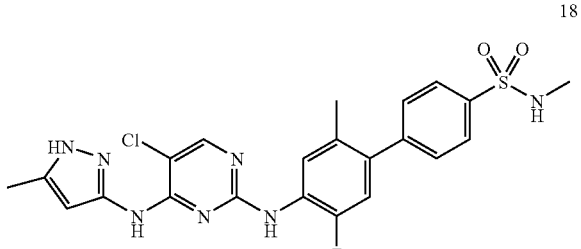

4'-(5-chloro-4-(5-methyl-1H-pyrazol-3-
ylamino)pyrimidin-2-ylamino)-5'-fluoro-N,2'-
dimethylbiphenyl-4-sulfonamide -continued

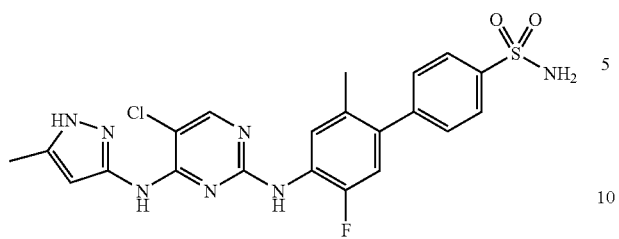

4'-(5-chloro-4-(5-methyl-1H-pyrazol-3-ylamino)pyrimidin-2-ylamino)-5'-fluoro-2'-methylbiphenyl-4-sulfonamide

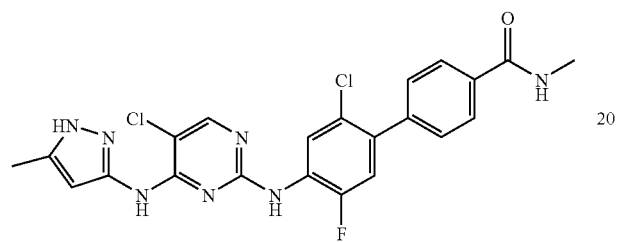

2'-chloro-4'-(5-chloro-4-(5-methyl-1H-pyrazol-3-ylamino)pyrimidin-2-ylamino)-5'-fluoro-N-methylbiphenyl-4-carboxamide

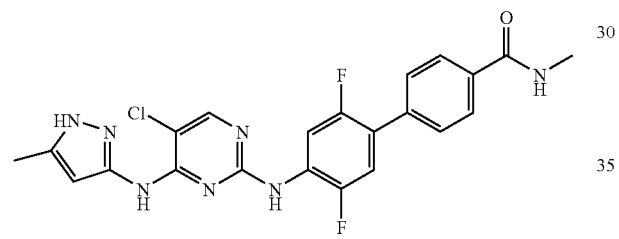

4'-(5-chloro-4-(5-methyl-1H-pyrazol-3-ylamino)pyrimidin-2-ylamino)-2',5'-difluoro-N-methylbiphenyl-4-carboxamide

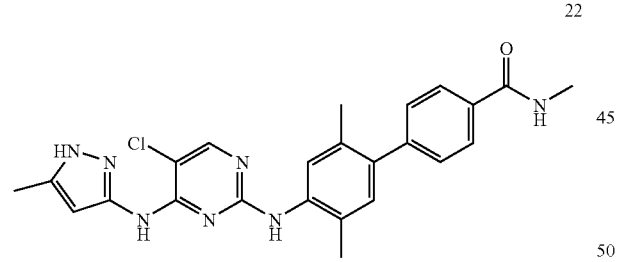

4'-(5-chloro-4-(5-methyl-1H-pyrazol-3-ylamino)pyrimidin-2-ylamino)-N,2',5'-trimethylbiphenyl-4-carboxamide

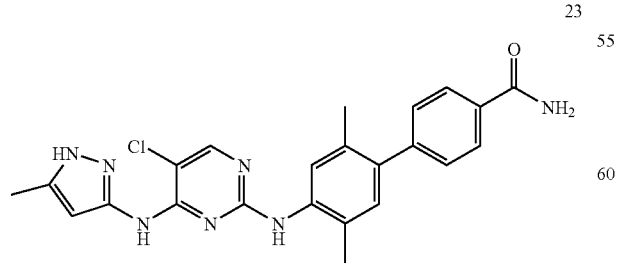

4'-(5-chloro-4-(5-methyl-1H-pyrazol-3-ylamino)pyrimidin-2-ylamino)-2',5'-dimethylbiphenyl-4-carboxamide -continued

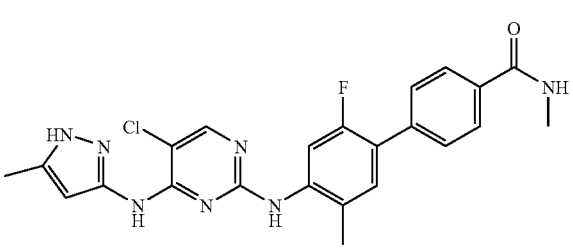

4'-(5-chloro-4-(5-methyl-1H-pyrazol-3-ylamino)pyrimidin-2-ylamino)-2'-fluoro-N,5'-dimethylbiphenyl-4-carboxamide 4'-(5-chloro-4-(5-methyl-1H-pyrazol-3-ylamino)pyrimidin-2-ylamino)-2'-isopropyl-N,5'-dimethylbiphenyl-4-carboxamide 4'-(5-chloro-4-(5-methyl-1H-pyrazol-3-ylamino)pyrimidin-2-ylamino)-N,2',3'-trimethylbiphenyl-4-carboxamide 5'-chloro-4'-(5-chloro-4-(5-methyl-1H-pyrazol-3-ylamino)pyrimidin-2-ylamino)-N,2'-dimethylbiphenyl-4-carboxamide

28

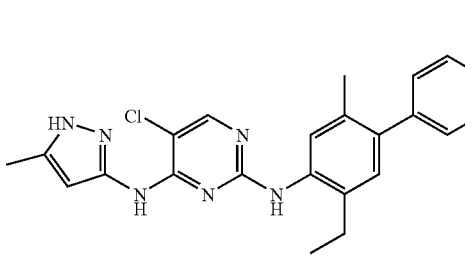

4'-(5-chloro-4-(5-methyl-1H-pyrazol-3-ylamino)pyrimidin-2-ylamino)-5'-ethyl-N,2'-dimethylbiphenyl-4-carboxamide

29

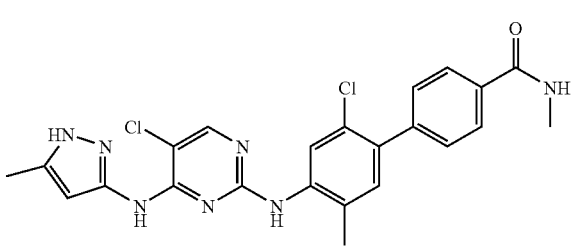

2'-chloro-4'-(5-chloro-4-(5-methyl-1H-pyrazol-3-ylamino)pyrimidin-2-ylamino)-N,5'-dimethylbiphenyl-4-carboxamide

30

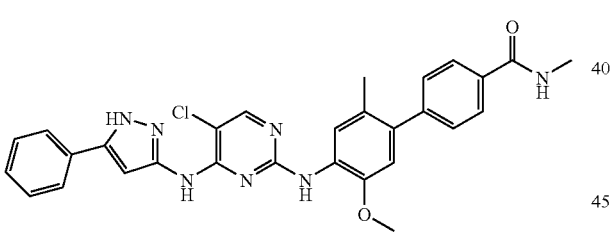

4'-(5-Chloro-4-(5-phenyl-1H-pyrazol-3-ylamino)pyrimidin-2-ylamino)-5'-methoxy-N,2'-dimethylbiphenyl-4-carboxamide

31

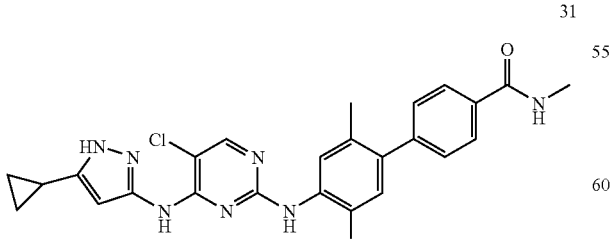

4'-(5-Chloro-4-(5-cyclopropyl-1H-pyrazol-3-ylamino)pyrimidin-2-ylamino)-5'-fluoro-N,2'-dimethylbiphenyl-4-carboxamide

32

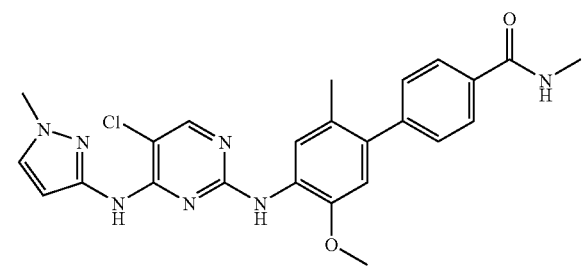

4'-(5-Chloro-4-(1-methyl-1H-pyrazol-3-ylamino)pyrimidin-2-ylamino)-5'-methoxy-N,2'-dimethylbiphenyl-4-carboxamide

33

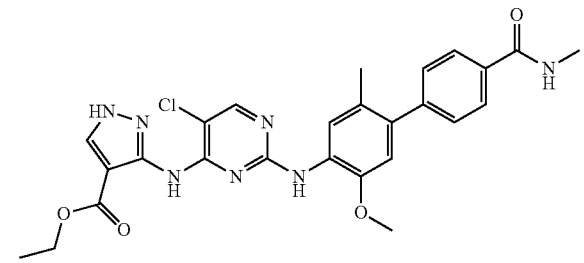

Ethyl 3-(5-chloro-2-(5-methoxy-2-methyl-4'-(methylcarbamoyl)biphenyl-4-ylamino)pyrimidin-4-ylamino)-1H-pyrazole-4-carboxylate

34

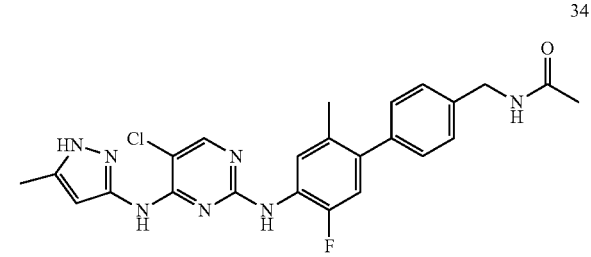

((4'-(5-chloro-4-(5-methyl-1H-pyrazol-3-ylamino)pyrimidin-2-ylamino)-5'-fluoro-2'-methylbiphenyl-4-yl)methyl)acetamide

37

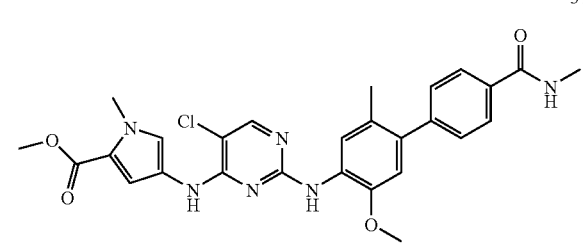

Methyl 4-(5-chloro-2-(5-methoxy-2-methyl-4'-(methylcarbamoyl)biphenyl-4-ylamino)pyrimidin-4-ylamino)-1-methyl-1H-pyrrole-2-carboxylate

38

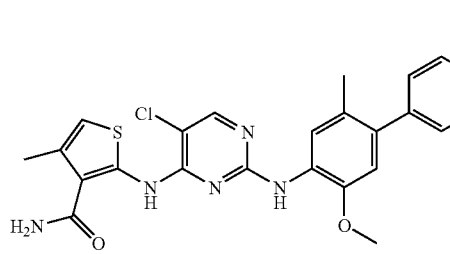

2-(5-Chloro-2-(5-methoxy-2-methyl-4′-(methylcarbamoyl)biphenyl-4-ylamino)pyrimidin-4-ylamino)-4-methylthiophene-3-carboxamide

39

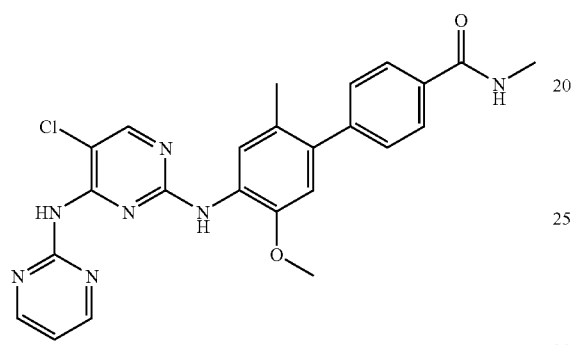

4′-(5-Chloro-4-(pyrimidin-2-ylamino)pyrimidin-2-ylamino)-5′-methoxy-N,2′-dimethylbiphenyl-4-carboxamide

40

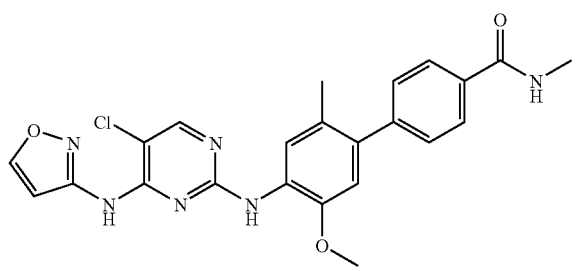

4′-(5-Chloro-4-(isoxazol-3-ylamino)pyrimidin-2-ylamino)-5′-methoxy-N,2′-dimethylbiphenyl-4-carboxamide

41

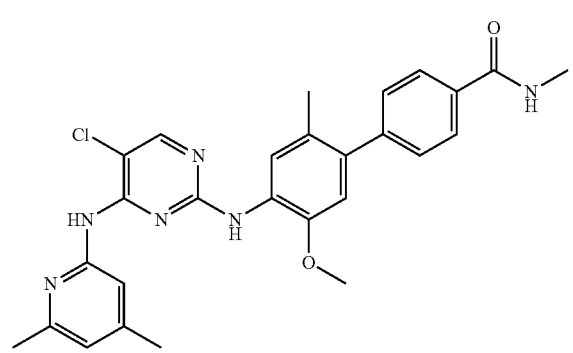

4′-(5-Chloro-4-(4,6-dimethylpyridin-2-ylamino)pyrimidin-2-ylamino)-5′-methoxy-N,2′-dimethylbiphenyl-4-carboxamide

42

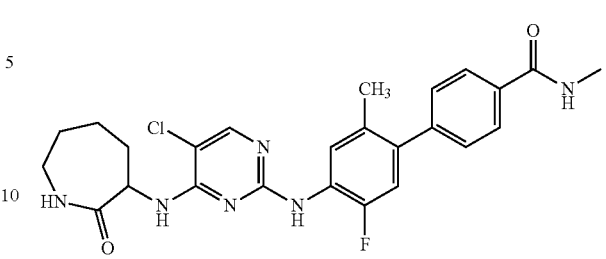

4′-(5-chloro-4-(2-oxoazepan-3-ylamino)pyrimidin-2-ylamino)-5′-fluoro-N,2′-dimethylbiphenyl-4-carboxamide

43

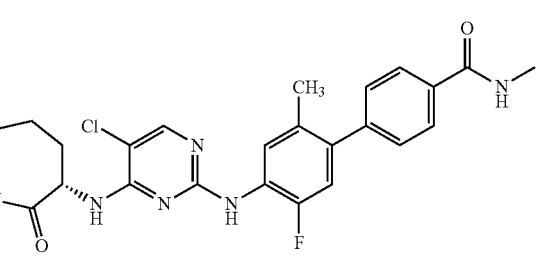

(S)-4′-(5-chloro-4-(2-oxoazepan-3-ylamino)pyrimidin-2-ylamino)-5′-fluoro-N,2′-dimethylbiphenyl-4-carboxamide

44

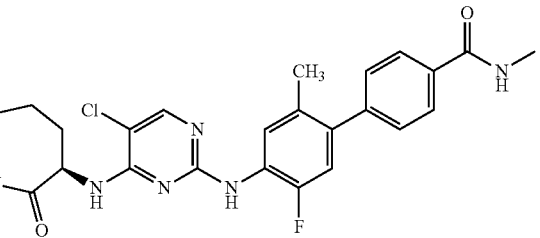

(R)-4′-(5-chloro-4-(2-oxoazepan-3-ylamino)pyrimidin-2-ylamino)-5′-fluoro-N,2′-dimethylbiphenyl-4-carboxamide

45

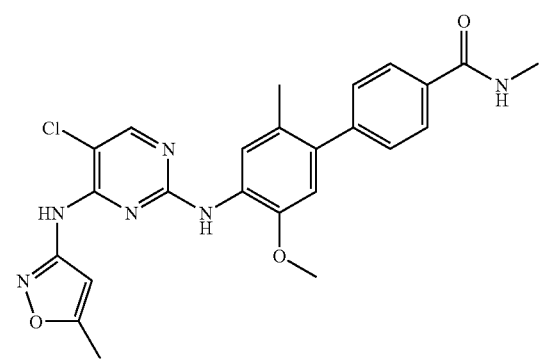

4′-(5-Chloro-4-(5-methylisoxazol-3-ylamino)pyrimidin-2-ylamino)-5′-methoxy-N,2′-dimethylbiphenyl-4-carboxamide

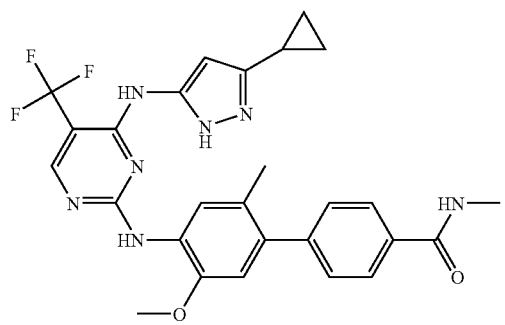

4'-(4-(3-cyclopropyl-1H-pyrazol-5-ylamino)-5-(trifluoromethyl)pyrimidin-2-ylamino)-5'-methoxy-N,2'-dimethylbiphenyl-4-carboxamide

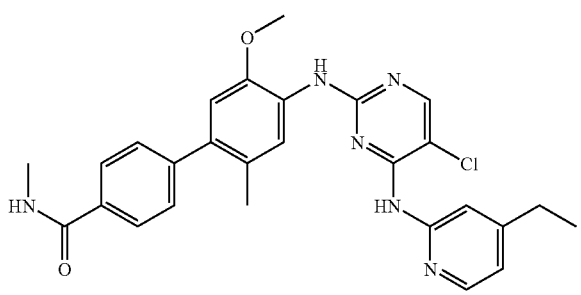

4'-(5-chloro-4-(4-ethylpyridin-2-ylamino)pyrimidin-2-ylamino)-5'-methoxy-N,2'-dimethylbiphenyl-4-carboxamide

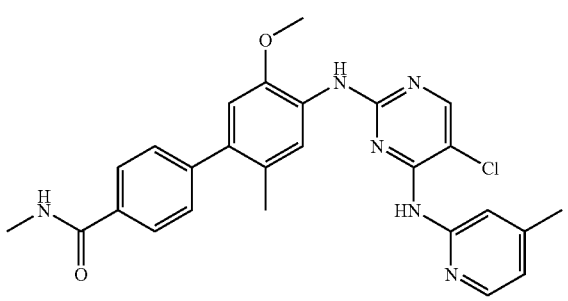

4'-(5-chloro-4-(4-methylpyridin-2-ylamino)pyrimidin-2-ylamino)-5'-methoxy-N,2'-dimethylbiphenyl-4-carboxamide

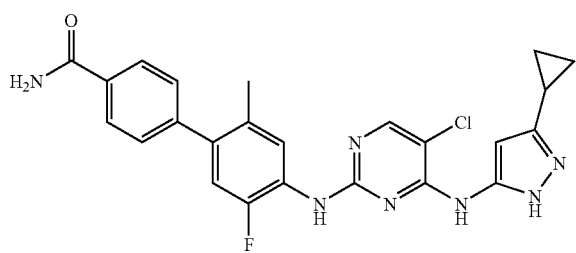

4'-(5-chloro-4-(3-cyclopropyl-1H-pyrazol-5-ylamino)pyrimidin-2-ylamino)-5'-fluoro-2'-methylbiphenyl-4-carboxamide

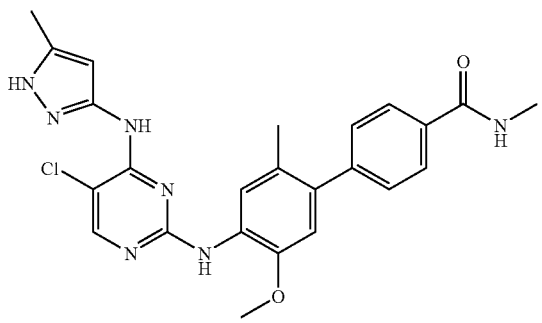

4'-(5-chloro-4-(5-methyl-1H-pyrazol-3-ylamino)pyrimidin-2-ylamino)-5'-methoxy-N,2'-dimethylbiphenyl-4-carboxamide

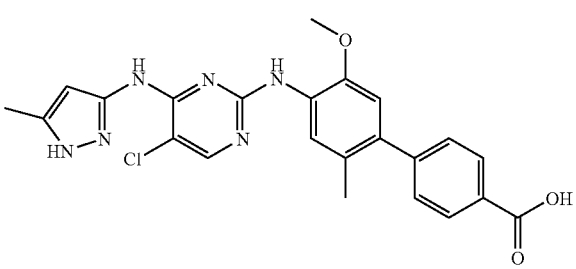

4'-(5-chloro-4-(5-methyl-1H-pyrazol-3-ylamino)pyrimidin-2-ylamino)-5'-methoxy-2'-methylbiphenyl-4-carboxylic acid

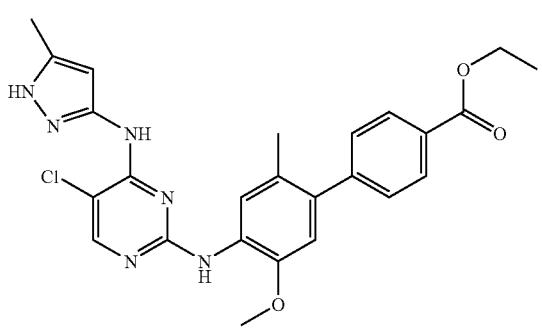

ethyl 4'-(5-chloro-4-(5-methyl-1H-pyrazol-3-ylamino)pyrimidin-2-ylamino)-5'-methoxy-2'-methylbiphenyl-4-carboxylate

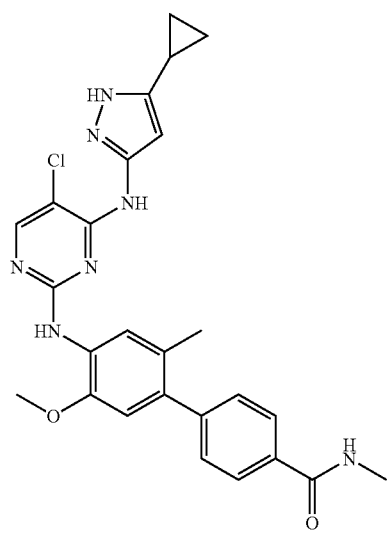

4'-(5-chloro-4-(5-cyclopropyl-1H-pyrazol-3-ylamino)pyrimidin-2-ylamino)-5'-methoxy-N,2'-dimethylbiphenyl-4-carboxamide

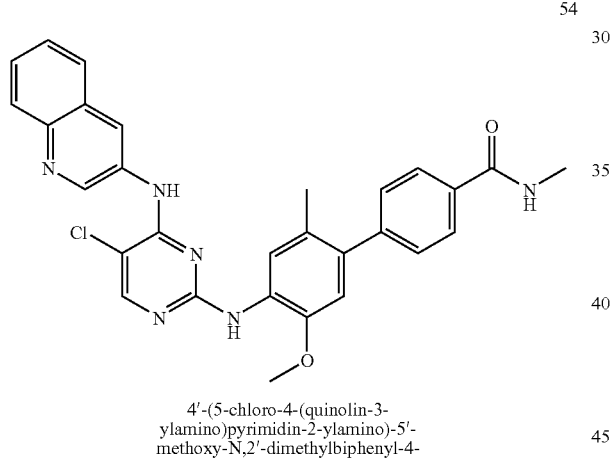

4'-(5-chloro-4-(quinolin-3-ylamino)pyrimidin-2-ylamino)-5'-methoxy-N,2'-dimethylbiphenyl-4-carboxamide

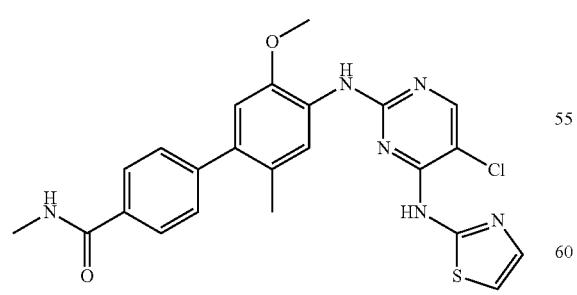

4'-(5-chloro-4-(thiazol-2-ylamino)pyrimidin-2-ylamino)-5'-methoxy-N,2'-dimethylbiphenyl-4-carboxamide

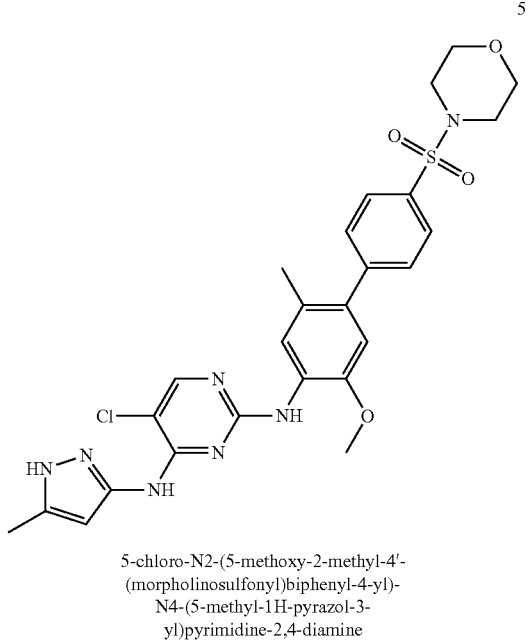

5-chloro-N2-(5-methoxy-2-methyl-4'-(morpholinosulfonyl)biphenyl-4-yl)-N4-(5-methyl-1H-pyrazol-3-yl)pyrimidine-2,4-diamine

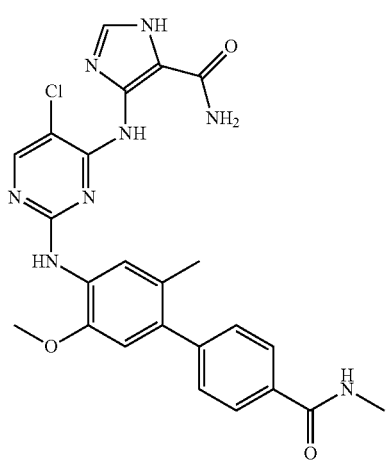

4-(5-chloro-2-(5-methoxy-2-methyl-4'-(methylcarbamoyl)biphenyl-4-ylamino)pyrimidin-4-ylamino)-1H-imidazole-5-carboxamide

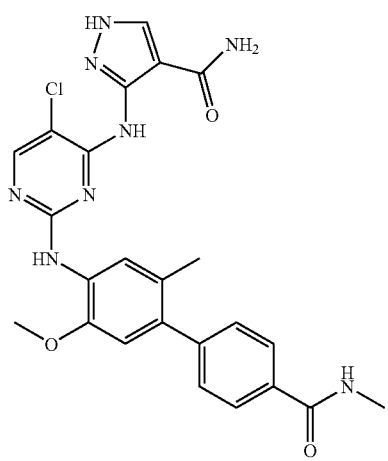

3-(5-chloro-2-(5-methoxy-2-methyl-4'-(methylcarbamoyl)biphenyl-4-ylamino)pyrimidin-4-ylamino)-1H-pyrazole-4-carboxamide

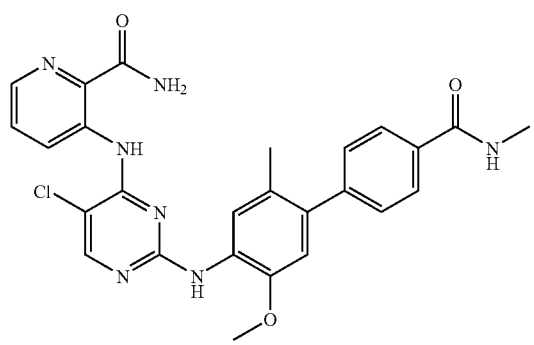

3-(5-chloro-2-(5-methoxy-2-methyl-4'-(methylcarbamoyl)biphenyl-4-ylamino)pyrimidin-4-ylamino)picolinamide

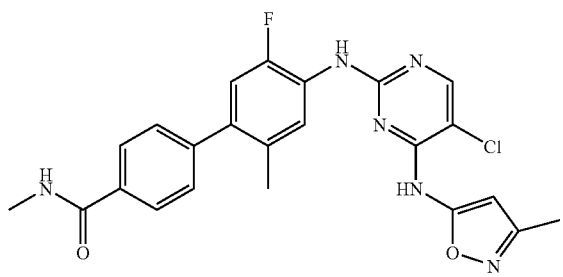

4'-(5-chloro-4-(3-methylisoxazol-5-ylamino)pyrimidin-2-ylamino)-5'-fluoro-N,2'-dimethylbiphenyl-4-carboxamide

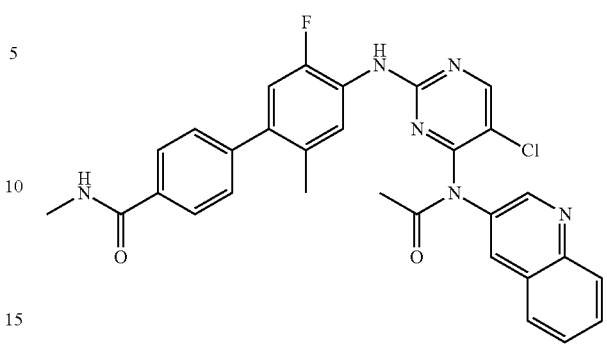

4'-(5-chloro-4-(N-(quinolin-3-yl)acetamido)pyrimidin-2-ylamino)-5'-fluoro-N,2'-dimethylbiphenyl-4-carboxamide

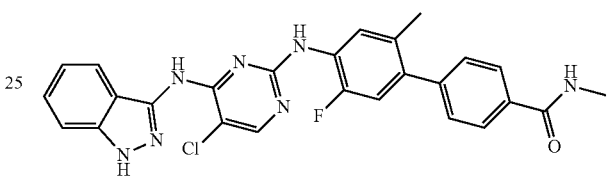

4'-(4-(1H-indazol-3-ylamino)-5-chloropyrimidin-2-ylamino)-5'-fluoro-N,2'-dimethylbiphenyl-4-carboxamide

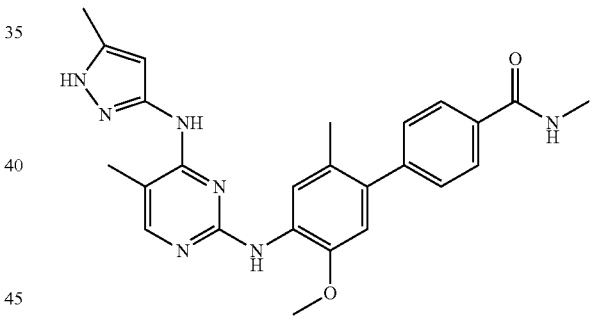

5'-methoxy-N,2'-dimethyl-4'-(5-methyl-4-(5-methyl-1H-pyrazol-3-ylamino)pyrimidin-2-ylamino)biphenyl-4-carboxamide

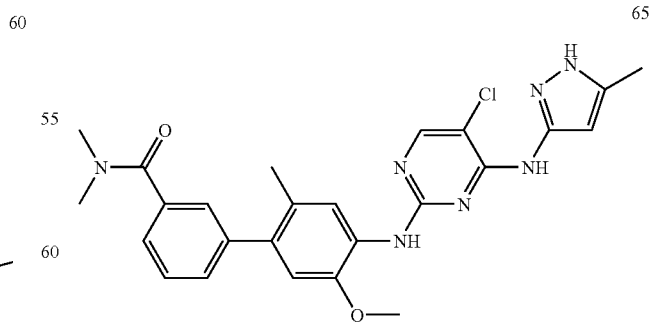

4'-(5-chloro-4-(5-methyl-1H-pyrazol-3-ylamino)pyrimidin-2-ylamino)-5'-methoxy-N,N,2'-trimethylbiphenyl-3-carboxamide

66

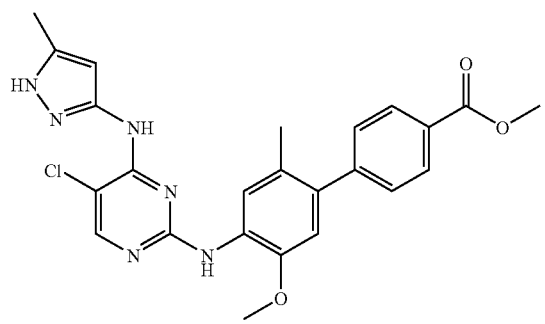

methyl 4'-(5-chloro-4-(5-methyl-1H-
pyrazol-3-ylamino)pyrimidin-2-
ylamino)-5'-methoxy-2'-
methylbiphenyl-4-carboxylate

67

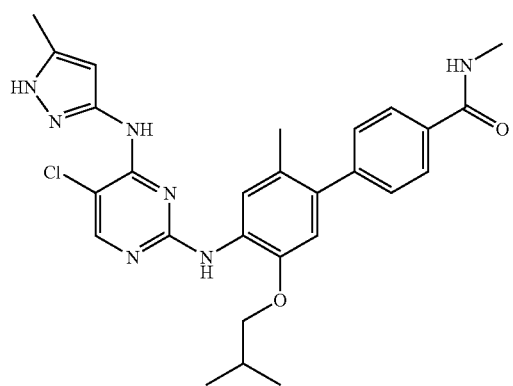

4'-(5-chloro-4-(5-methyl-1H-pyrazol-3-
ylamino)pyrimidin-2-ylamino)-5'-
isobutoxy-N,2'-dimethylbiphenyl-4-
carboxamide

68

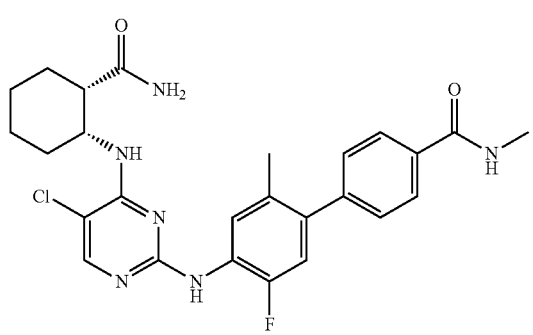

4'-(4-((1R,2S)-2-
carbamoylcyclohexylamino)-5-
chloropyrimidin-2-ylamino)-5'-fluoro-
N,2'-dimethylbiphenyl-4-carboxamide

69

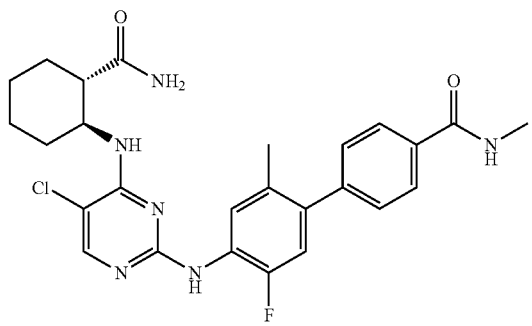

4'-(4-((1S,2S)-2-
carbamoylcyclohexylamino)-5-
chloropyrimidin-2-ylamino)-5'-fluoro-
N,2'-dimethylbiphenyl-4-carboxamide;
and

70

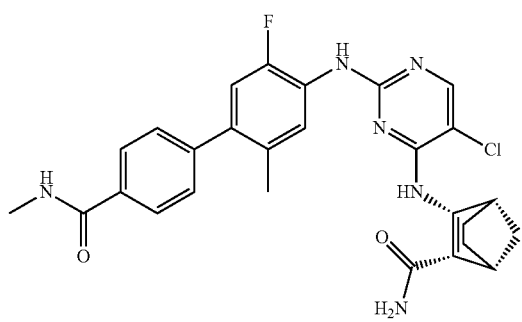

(1R,2S,3R,4S)-3-(5-chloro-2-(5-fluoro-
2-methyl-4'-
(methylcarbamoyl)biphenyl-4-
ylamino)pyrimidin-4-
ylamino)bicyclo[2.2.1]hept-5-ene-2-
carboxamide;

or a pharmaceutically acceptable salt thereof.

7. A pharmaceutical composition comprising a therapeutically effective amount of a compound of claim 1 and a pharmaceutically acceptable carrier.

* * * * *